US005856459A

United States Patent [19]
Frank et al.

[11] Patent Number: 5,856,459
[45] Date of Patent: Jan. 5, 1999

[54] OLIGONUCLEOTIDES SPECIFIC FOR HEPATITIS B VIRUS

[75] Inventors: Bruce L. Frank, Marlborough; Peter C. Roberts, Holliston; John Goodchild, Westborough, all of Mass.; J. Charles Craig; John S. Mills, both of Welwyn Garden, United Kingdom

[73] Assignee: Hybridon, Inc., Cambridge, Mass.

[21] Appl. No.: 468,352

[22] Filed: Jun. 6, 1995

Related U.S. Application Data

[62] Division of Ser. No. 467,397, Jun. 6, 1995, abandoned.

[51] Int. Cl.⁶ .................................................. C07H 21/00
[52] U.S. Cl. ............................................................ 536/24.5
[58] Field of Search ............................. 536/24.5; 514/44

[56] References Cited

FOREIGN PATENT DOCUMENTS

WO 92/06693  4/1992  WIPO .
WO 94/24864  11/1994  WIPO .

OTHER PUBLICATIONS

Orkin et al. (1995) *Report and Recommendations of the Panel to Assess the NIH Investment in Research on Gene Therapy*.
Korba et al. Antisense oligonucleotides are effective inhibitors of hepatitis B virus replication in vitro Antiviral Research vol. 28 225–242, 1995.
Gura Antisense has growing pains Science vol. 270 575–577, 1995.
Sureau et al. (1986) *Cell* 47:37–47.
Sells et al. (1987) *Proc. Nat. Acad. Sci.* 84:1005–1009.
Goodarzi et al. (1990) *J. Gen. Virol.* 71:3021–3025.
Blum et al. (1991) *Lancet* 337:1230.
Doong et al. (1991) *Proc. Natl. Acad. Sci. (USA)* 88:8495–8499.
Korba et al. (1992) *Antiviral Res.* 19:55–70.
Wu et al. (1992) *J. Biol. Chem.* 267:12436–12439.
Jansen et al. (1993) *Antimicrob. Agent. Chemother.* 37:441–447.
Offensperger et al. (1993) *EMBO J.* 12:1257–1262.
Reinis et al. (1993) *Folia Biologica* (Praha) 39:262–269.
Yao et al. (1994) *Nat. Med. J. China* 74:125.

*Primary Examiner*—James Ketter
*Assistant Examiner*—John S. Brusca
*Attorney, Agent, or Firm*—Hale and Dorr LLP

[57] ABSTRACT

The present invention discloses synthetic oligonucleotides complementary to contiguous and noncontiguous regions of the HBV RNA. Also disclosed are methods and kits for inhibiting the replication and expression of HBV, and for treating HBV infections and associated conditions.

21 Claims, 11 Drawing Sheets

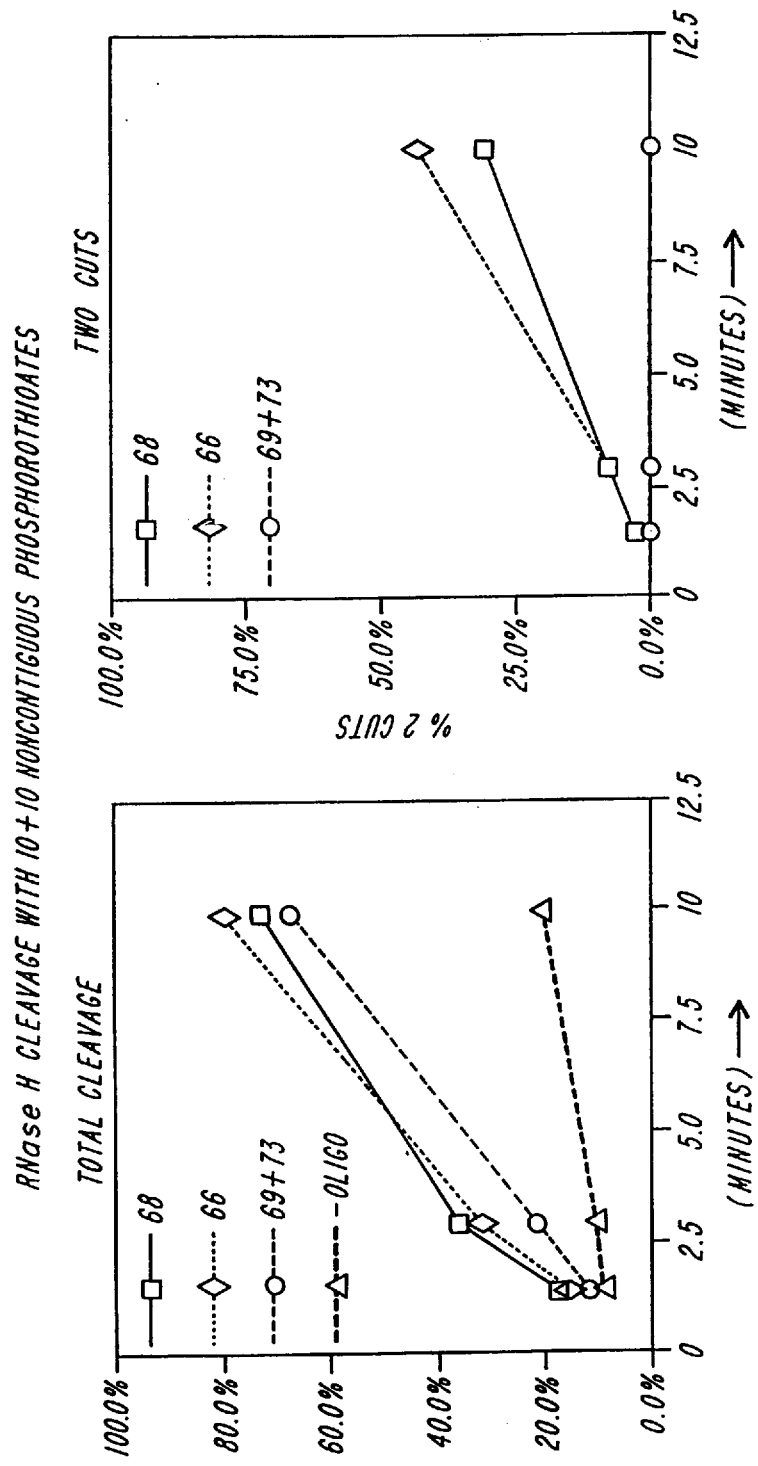

ALTERNATE HBV EPSILON TARGETS FOR PRIMARY ASSAYS
pGLE
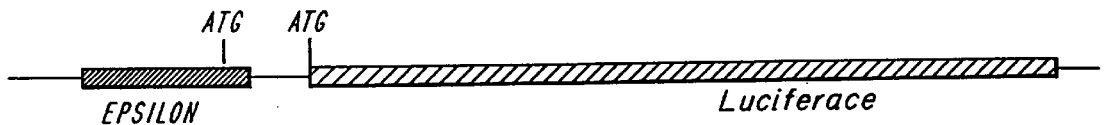
pGLE2
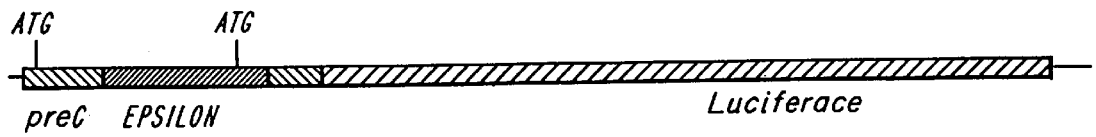
pGLE3
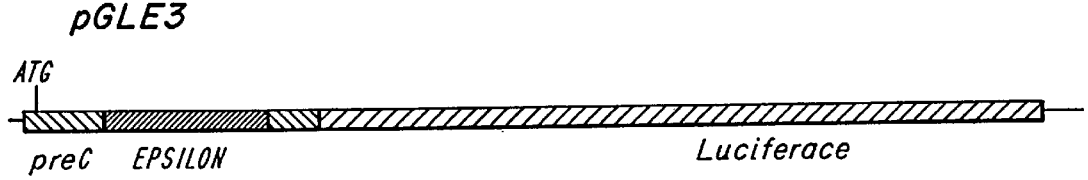
pGLpol
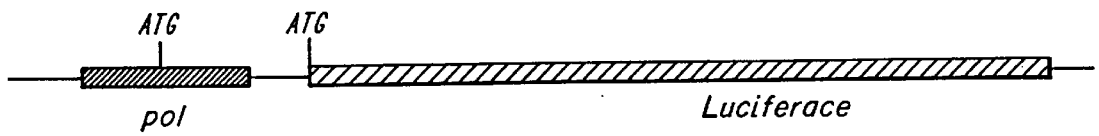
FIG. 10

TRUNCATED POL REPRESENTS -17 TO +634 OF THE POL OPEN READING FRAME. THE NORMAL LEUCINE CODON AT +635 TO +637 HAS BEEN REPLACED BY A STOP CODON.

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:1:

G G T G C G C A G A     C C A A T T T A T G                      2 0

( 2 ) INFORMATION FOR SEQ ID NO:2:

( i ) SEQUENCE CHARACTERISTICS:

(A) LENGTH: 19 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:2:

CATGGTGCTG GTGCGCAGA                                                          19

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:3:

GAAAAAGTTG CATGGTGCTG                                                         20

(2) INFORMATION FOR SEQ ID NO:4:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:4:

GAGGTGAAAA AGTTGCATGG                                                         20

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:5:

AGGCAGAGGT GAAAAAGTTG                                                         20

(2) INFORMATION FOR SEQ ID NO:6:

(i) SEQUENCE CHARACTERISTICS:
(A) LENGTH: 12 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:6:

AGGCAGAGGT GA 12

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:7:

AGAGATGATT AGGCAGAGGT 20

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:8:

GACATGAACA AGAGATGATT AGGCAGAGGT 30

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:9:

GACATGTACA AGAGATGATT 20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO ( i v ) ANTI-SENSE: YES ( x i ) SEQUENCE DESCRIPTION: SEQ ID NO:10:

GTAGGACATG AACAAGAGAT    20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:11:

TTGGAGGCTT GAACAGTAGG    20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:12:

CACAGCTTGG AGGCTTGAAC    20

( 2 ) INFORMATION FOR SEQ ID NO:13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:13:

AGCCACCCAA GGCACAGCTT    20

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:14:

TCGATGTCCA TGCCCCAAAG                                                                                          20

( 2 ) INFORMATION FOR SEQ ID NO:15:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:15:

TAAGGGTCGA TGTCCATGCC                                                                                          20

( 2 ) INFORMATION FOR SEQ ID NO:16:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:16:

TTATAAGGGT CGATGTCCAT                                                                                          20

( 2 ) INFORMATION FOR SEQ ID NO:17:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:17:

AAATTCTTTA TAAGGGTCGA TGTCCAT                                                                                  27

( 2 ) INFORMATION FOR SEQ ID NO:18:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:18:

TATAAGGGTC GA                                                                                                  12

( 2 ) INFORMATION FOR SEQ ID NO:19:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:19:

AAATTCTTTA TAAGGGTCGA                                                            20

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:20:

GTATCTAGAA GATCTCGTAC                                                            20

( 2 ) INFORMATION FOR SEQ ID NO:21:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:21:

GCGGTGTCTA GAAGATCTCG                                                            20

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:22:

GAGGCGGTGT CTAGGAGATC                                                            20

( 2 ) INFORMATION FOR SEQ ID NO:23:

( i ) SEQUENCE CHARACTERISTICS:
    ( A ) LENGTH: 20 base pairs (B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:23:

GAGCTGAGGC GGTGTCTAGG    20

(2) INFORMATION FOR SEQ ID NO:24:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:24:

ATACAGAGCT GAGGCGGTAT    20

(2) INFORMATION FOR SEQ ID NO:25:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:25:

TCCCGATACA GAGCTGAGGC    20

(2) INFORMATION FOR SEQ ID NO:26:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:26:

AGGCTTCCCG ATACAGAGCT    20

(2) INFORMATION FOR SEQ ID NO:27:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:27:

ACAATGCTCA GGAGACTCTA 20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:28:

GCAGTATGGT GAGGTGAGCA 20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:29:

GAGTGCAGTA TGGTGAGGTG 20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: YES (x i) SEQUENCE DESCRIPTION: SEQ ID NO:30:

TGCCTGAGTG CAGTATGGTG 20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (iv) ANTI-SENSE: YES (xi) SEQUENCE DESCRIPTION: SEQ ID NO:31:

TTGCTTGCCT GAGTGCAGTA 20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:32:

TAAGGGTCGA AGAGATGATT 20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:33:

AGAGATGATT TAAGGGTCGA 20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:34:

TAAGGGTCGA AGGCAGAGGT 20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:35:

AGGCAGAGGT TAAGGGTCGA 20

( 2 ) INFORMATION FOR SEQ ID NO:36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:36:

TATAAGGGTC GAAGGCAGAG GTGA 24

( 2 ) INFORMATION FOR SEQ ID NO:37:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:37:

AGGCAGAGGT GATATAAGGG TCGA 24

( 2 ) INFORMATION FOR SEQ ID NO:38:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:38:

AGAGATGATT AGGCAGAGGT TAAGGGTCGA 30

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:39:

GACATGAACA AGAGATGATT TAAGGGTCGA 30

( 2 ) INFORMATION FOR SEQ ID NO:40:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:40:

AGAGATGATT TAAGGGTCGA TGTCCATGCC 30

( 2 ) INFORMATION FOR SEQ ID NO:41:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:41:

AGGCAGAGGT TAAGGGTCGA TGTCCATGCC 30

( 2 ) INFORMATION FOR SEQ ID NO:42:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:42:

GGCATTTGGT GGTCTATAAG 20

( 2 ) INFORMATION FOR SEQ ID NO:43:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:43:

GATAGGGGCA TTTGGTGGTC 20

( 2 ) INFORMATION FOR SEQ ID NO:44:

( i ) SEQUENCE CHARACTERISTICS:
  ( A ) LENGTH: 20 base pairs
  ( B ) TYPE: nucleic acid ( C ) STRANDEDNESS: single
( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:44:

TGTTGATAGG ATAGGGGCAT  20

( 2 ) INFORMATION FOR SEQ ID NO:45:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:45:

ACCCAAGGCA CAGCTTGGAG  20

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:46:

GACAGGGGCA TTTGGTGGTC  20

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:47:

GATAGGGGCC TTTGGTGGTC  20

( 2 ) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:48:

GATAGGGGCA TTTGGTGCTC 20

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:49:

GACAGGGGCC TTTGGTGCTC 20

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:50:

ATGTTTTTGG CGTCTTCCAT 20

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:51:

TGCTGGGGGG AACTAATGAC T 21

( 2 ) INFORMATION FOR SEQ ID NO:52:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:52:

GGAGTGCGAA TCCACACTCC GAAAG 25

( 2 ) INFORMATION FOR SEQ ID NO:53:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:53:

TAAGGGTCGA 10

( 2 ) INFORMATION FOR SEQ ID NO:54:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:54:

AGGCAGAGGT 10

( 2 ) INFORMATION FOR SEQ ID NO:55:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:55:

ATATTCGCAC GAATTCAGCT TATAGACCAC CAAATG 36

( 2 ) INFORMATION FOR SEQ ID NO:56:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO -continued (iv) ANTI-SENSE: NO (xi) SEQUENCE DESCRIPTION: SEQ ID NO:56:

GTTGGGATTG CTGCAGCTAT CTGGATTTGC GGTG 34

OLIGONUCLEOTIDES SPECIFIC FOR HEPATITIS B VIRUS

CROSS-REFERENCE TO RELATED APPLICATIONS

This application is related to patent application Ser. Nos. 08/463,624, filed Jun. 6, 1995, now abandoned, and 08/467,398, filed Jun. 6, 1995 now abandoned, and is a divisional of application Ser. No. 08/467,397, filed Jun. 6, 1995, now abandoned, each entitled "OLIGONUCLEOTIDES SPECIFIC FOR HEPATITIS B VIRUS", filed on even date, and assigned to the present assignees.

FIELD OF THE INVENTION

This invention relates to hepatitis B virus. More particularly, this invention relates to the control of hepatitis B viral expression and replication using oligonucleotides complementary to particular regions of hepatitis B virus nucleic acid.

BACKGROUND OF THE INVENTION

Hepatitis B virus (HBV) is a compact, enveloped DNA virus belonging to the Hepadnavirus family. This virus is the major cause of chronic liver disease and hepatocellular carcinoma world-wide (Hoofnagle (1990) *N. Eng. J. Med.* 323:337–339). HBV is associated with acute and chronic hepatitis and hepatocellular carcinoma, and may also be a cofactor in the development of acquired immune deficiency syndrome (Dienstag et al. in *Harrison's Principles of Internal Medicine,* 13th Ed. (Isselbacher et al., eds.) McGraw-Hill, NY, N.Y. (1993) pp. 1458–1483). At least 400 million people worldwide are currently infected with HBV.

There is no known treatment for acute hepatitis. Antiviral therapy with interferon-a has been used for chronic hepatitis, but has met with only partial success, and there are complications from such therapy. Short term therapy with glucocorticoids may be beneficial in conjunction with interferon therapy, but long term treatment is limited by toxicological problems (Dienstag et al. in *Harrison's Principles of Internal Medicine,* 13th Ed. (Isselbacher et al., eds.) McGraw-Hill, NY, N.Y. (1993) pp. 1458–1483). Thus, emphasis has been placed on prevention through immunization.

New chemotherapeutic agents have been developed which are capable of modulating cellular and foreign gene expression (see, Zamecnik et al. (1978) *Proc. Natl. Acad. Sci.* (USA) 75:280–284; Zamecnik et al. (1986) *Proc. Natl. Acad. Sci.* (USA) 83:4143–4146; Goodchild et al. (1988) *Proc. Natl. Acad. Sci.* (USA) 85:5507–5511). These agents, called antisense oligonucleotides, bind to target single-stranded nucleic acid molecules according to the Watson-Crick rule or to double-stranded nucleic acids by the Hoogsteen rule of base pairing, and in so doing, disrupt the function of the target by one of several mechanisms: by preventing the binding of factors required for normal transcription, splicing, or translation; by triggering the enzymatic destruction of mRNA by RNase H, or by destroying the target via reactive groups attached directly to the antisense oligonucleotide.

Improved oligonucleotides have more recently been developed that have greater efficacy in inhibiting such viruses, pathogens and selective gene expression. Some of these oligonucleotides having modifications in their internucleotide linkages have been shown to be more effective than their unmodified counterparts. For example, Agrawal et al. (*Proc. Natl. Acad. Sci.* (USA) (1988) 85:7079–7083) teaches that oligonucleotide phosphorothioates and certain oligonucleotide phosphoramidates are more effective at inhibiting HIV-1 than conventional phosphodiester-linked oligodeoxynucleotides. Agrawal et al. (*Proc. Natl. Acad. Sci.* (USA) (1989) 86:7790–7794) discloses the advantage of oligonucleotide phosphorothioates in inhibiting HIV-1 in early and chronically infected cells.

In addition, chimeric oligonucleotides having more than one type of internucleotide linkage within the oligonucleotide have been developed. Pederson et al. (U.S. Pat. Nos. 5,149,797 and 5,220,007) discloses chimeric oligonucleotides having an oligonucleotide phosphodiester or oligonucleotide phosphorothioate core sequence flanked by nucleotide methylphosphonates or phosphoramidates. Furdon et al. (*Nucleic Acids Res.* (1989) 17:9193–9204) discloses chimeric oligonucleotides having regions of oligonucleotide phosphodiesters in addition to either oligonucleotide phosphorothioate or methylphosphonate regions. Quartin et al. (*Nucleic Acids Res.* (1989) 17:7523–7562) discloses chimeric oligonucleotides having regions of oligonucleotide phosphodiesters and oligonucleotide methylphosphonates. Inoue et al. (*FEBS Lett.* (1987) 215:237–250) discloses hybrid oligonucleotides having regions of deoxyribonucleotides and 2'-O-methyl-ribonucleotides.

Antisense oligonucleotides have been designed which inhibit the expression and/or replication of HBV. For example, antisense oligonucleotides directed against the cap site of HBV mRNA transcribed from the SPII promoter (Goodarzi et al. (1990) *J. Gen. Virol.* 71:3021–3025; Yao et al. (1994) *Nat. Med. J. China* 74:125), against the translational initiation site of the S gene (Yao et al. (1994) *Nat. Med. J. China* 74:125; Reinis et al. (1993) *Folia Biologica* (Praha) 39:262–269; Goodarzi et al. (1990) *J. Gen. Virol.* 71:3021–3025); against a portion of the core-pol mRNA encoding the terminal protein region of the viral polymerase (WO 94/24864; Blum et al. (1991) *Lancet* 337:1230), and against the HBV polyadenylation signal (Wu et al. (1992) *J. Biol. Chem.* 267:12436–12439) have been designed. In addition, phosphorothioate oligodeoxynucleotides prepared against the 5' region of the pre-S gene have been shown to inhibit duck HBV replication and gene expression in vivo (Offensperger et al. (1993) *EMBO J.* 12:1257–1262).

A need still remains for the development of oligonucleotides that are capable of inhibiting the replication and expression of HBV whose administration are accompanied by a good prognosis and low or no cellular toxicity.

SUMMARY OF THE INVENTION

It has been discovered that specific oligonucleotides complementary to particular contiguous and noncontiguous portions of pregenomic and messenger RNA encoding the precore, core, and polymerase proteins of HBV can inhibit HBV replication, packaging, and expression. This discovery has been exploited to provide synthetic oligonucleotides complementary to various contiguous and noncontiguous regions of HBV RNA.

As used herein, a "synthetic oligonucleotide" includes chemically synthesized polymers of about five and up to about 50, preferably from about 15 to about 30 ribonucleotide and/or deoxyribonucleotide monomers connected together or linked by at least one, and preferably more than one, 5' to 3' internucleotide linkage.

For purposes of the invention, the term "oligonucleotide sequence that is complementary to RNA" is intended to mean an oligonucleotide that binds to the nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means, including in the case of an oligonucleotide binding to RNA, causing pseudoknot formation. Binding by Watson-Crick or Hoogsteen base pairing under physiological conditions is measured as a practical matter by observing interference with the function of the nucleic acid sequence.

In a first aspect, the invention provides synthetic oligonucleotides complementary to a portion of the HBV RNA and having a nucleotide sequence selected from the group consisting of SEQ ID NOS:1–31 and 42–48.

In another aspect, the invention provides synthetic oligonucleotides complementary to at least two noncontiguous regions of an HBV nucleic acid. In preferred embodiments, the two noncontiguous regions to which the oligonucleotides of the invention are complementary are in the epsilon region of the precore gene. As used herein, the "epsilon region" is meant to encompass the stem-loop and flanking base sequences of the pregenomic RNA, precpre mRNA, and core-pol mRNA, and includes nucleotides (nt) 1827–1921. In some embodiments, these oligonucleotides are about 20 to about 30 nucleotides in length. In some embodiments, noncontiguous oligonucleotides of the invention include a sequence selected from the group consisting of SEQ ID NOS:32–41.

In some embodiments, the oligonucleotides of the invention are modified. These modifications, in some embodiments, include at least one alkylphosphonate, phosphorothioate, phosphorodithioate, alkylphosphonothioate, phosphoramidate, carbamate, carbonate, phosphate triester, acetamidate, or carboxymethyl ester internucleotide linkage or a combination of such linkages, as in a chimeric oligonucleotide. In one preferred embodiment, an oligonucleotide of the invention includes phosphorothioate internucleotide linkages.

In some embodiments, the oligonucleotides of the invention also include at least one ribonucleotide, at least one deoxyribonucleotide, or a combination thereof, as in a hybrid oligonucleotide. An oligonucleotide containing at least one 2'-O-methyl ribonucleotide is another embodiment of the invention.

In other aspects, the invention provides a pharmaceutical composition comprising at least one contiguous or noncontiguous HBV-specific oligonucleotide of the invention as described above, and in some embodiments, this composition includes at least two different oligonucleotides (i.e., having a different nucleotide sequence, length, and/or modification(s)). The pharmaceutical composition of some embodiments is a physical mixture of at least two, and preferably, many oligonucleotides with the same or different sequences, modifications, and/or lengths. In some embodiments, this pharmaceutical formulation also includes a physiologically or pharmaceutically acceptable carrier.

Another aspect of the invention are kits for inhibiting HBV replication and/or infection in a cell. In preferred embodiments, the kits include at least one contiguous or noncontiguous oligonucleotide of the invention, or a combination thereof. In other preferred embodiments, at least two synthetic oligonucleotides of the invention are in the kit.

In yet another aspect of the invention, a therapeutic amount of a pharmaceutical composition containing HBV-specific synthetic oligonucleotides is administered to the cell in a method of inhibiting HBV replication. The HBV-specific oligonucleotides are the contiguous or noncontiguous oligonucleotides of the invention. In some preferred embodiments, the method includes administering at least one oligonucleotide, or at least two oligonucleotides, having a sequence set forth in the Sequence Listing as SEQ ID NO:1–31, 32–41, or 42–48, or a combination thereof.

In another aspect, a method of treating HBV infection is provided, comprising the step of administering to an infected animal, including a human, or cell, a therapeutic amount of a pharmaceutical composition containing at least one HBV-specific oligonucleotide, and in some embodiments, at least two HBV-specific oligonucleotides. The HBV-specific oligonucleotides are contiguous or non-contiguous. In preferred embodiments, the oligonucleotides administered have a sequence set forth in the Sequence Listing as SEQ ID NO:1–31, 32–41, or 42–48, or a combination thereof.

In all methods involving the administration of oligonucleotide(s) of the invention, at least one, and preferably two or more identical or different oligonucleotides may be administered simultaneously or sequentially as a single treatment episode in the form of separate pharmaceutical compositions.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 5A is a graphic representation showing the results of RNase H cleavage in the presence of noncontiguous oligonucleotides having 10 nucleotides complementary to the 5' side (site 1) of the epsilon region and 10 nucleotides complementary to the 3' side of the epsilon region (10+10);

FIG. 5B is a graphic representation showing the results of RNase H cleavage with 10+10 noncontiguous oligonucleotides (two cuts);

FIG. 10 is a schematic representation of the HBV-luciferase fusion targets used for luciferase assays;

DETAILED DESCRIPTION OF THE PREFERRED EMBODIMENTS

The patent and scientific literature referred to herein establishes the knowledge that is available to those with skill in the art. The issued U.S. patents, allowed applications, published foreign applications, and references cited herein are hereby incorporated by reference.

HBV is a compact, enveloped DNA virus belonging to the Hepadnavirus family. It has a circular, partially single-stranded, partially double-stranded 3.2 kb genome which includes four overlapping genes: (1) the pre-S and S genes, which encode the various envelope or surface antigens (HBsAg); (2) the preC and C gene, which encodes the antigens HBcAg and HBeAg; (3) the P gene, which encodes the viral polymerase; and (4) the X gene, which encodes HBx, the transactivating protein. Full-length clones of many hepadnaviruses have been obtained and their nucleotide sequences obtained. (see, e.g., Raney et al. in *Molecular Biology of the Hepatitis B Virus* (McLachlan, ed.) CRC Press, Boston, Mass., (1991) pp. 1–38). Replication occurs in hepatocytes and involves converting the single stranded-region of the HBV genome to double-stranded circular DNA, generating the covalently closed circular (CCC) DNA. Transcription of this DNA by the host RNA polymerase generates an RNA template of plus stranded polarity, the pregenomic RNA, which serves as a template for the translation of viral proteins, and is also encapsidated into virus cores. In the virus cores, the RNA serves as a template for reverse transcription, generating a DNA minus strand. The viral polymerase then produces a DNA plus strand using an oligomer of viral RNA as a primer. The newly synthesized double-stranded DNA in the viral core is assembled with the viral envelope proteins, generating a newly infectious viral particle.

Antisense oligonucleotide technology provides a novel approach to the inhibition of HBV expression, and hence, to the treatment or prevention of acute and chronic hepatitis and hepatocellular carcinoma (see generally, Agrawal (1992) *Trends Biotech.* 10:152; and Crooke (*Proc. Am. Ass. Cancer Res. Ann. Meeting* (1995) 36:655). By binding to the complementary nucleic acid sequence, antisense oligonucleotides are able to inhibit splicing and translation of RNA, and replication of genomic RNA. In this way, antisense oligonucleotides are able to inhibit protein expression.

Figure 1A:
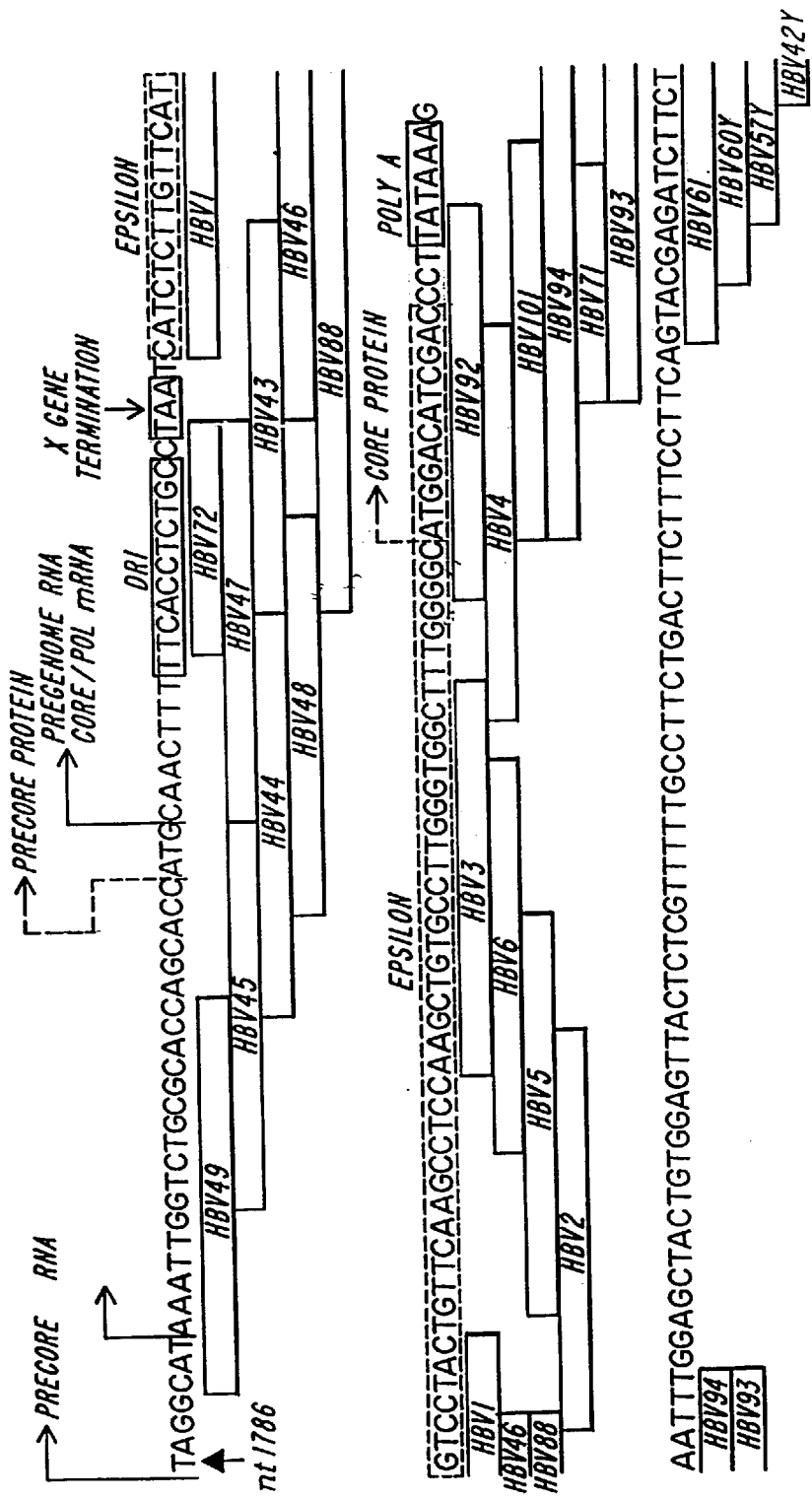
FIG. 1A is a schematic representation showing contiguous oligonucleotides of the invention targeted to various functional regions of the HBV ayw sequence from nt 1786–2328.
Figure 1B:
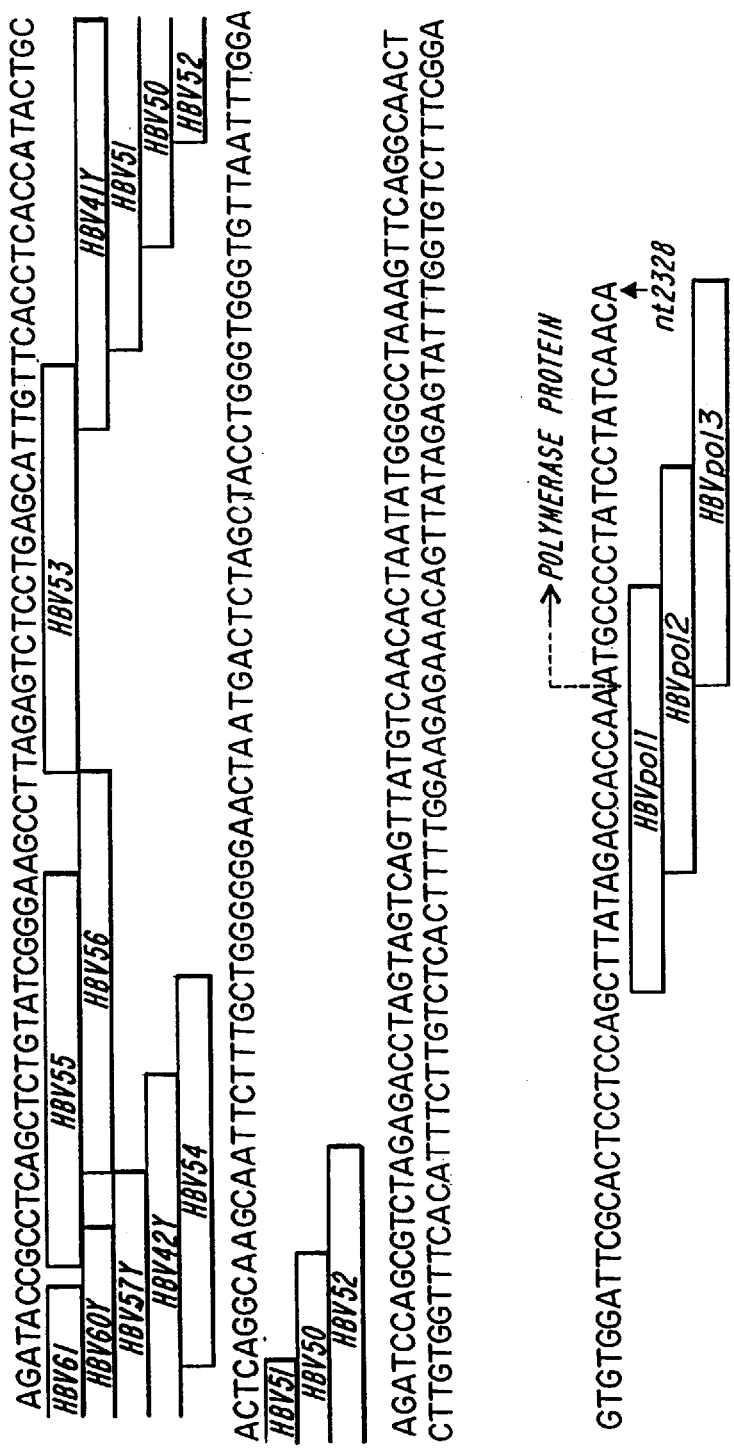
FIG. 1B is a continuation of FIG. 1A, which is a schematic representation showing contiguous oligonucleotides of the invention targeted to various functional regions of the HBV ayw sequence from nt 1786–2328.

Synthetic "contiguous" oligonucleotides of the invention, or oligonucleotides targeted to contiguous regions of HBV precore mRNA, core/pol mRNA, and pregenomic RNA (FIG. 1) are complementary to sequences encoding the precore region, to sequences spanning the precore and core regions, to sequences including the polymerase translation initiation region, and to regions within the epsilon region. Representative contiguous oligonucleotides of the invention are set forth below in Table 1.

TABLE 1

| OLIGO | Sequence (5' → 3') | Position | Chemistry | SEQ ID NO: |
|---|---|---|---|---|
| HBV49[a] | GGTGCGCAGACCAATTTATG | 1790–1809 | DNA PS | 1 |
| HBV45[a] | CATGGTGCTGGTGCGCAGA | 1799–1818 | DNA PS | 2 |
| HBV44[a] | GAAAAAGTTGCATGGTGCTG | 1809–1828 | DNA PS | 3 |
| HBV48[a] | GAGGTGAAAAAGTTGCATGG | 1814–1833 | DNA PS | 4 |
| HBV47[a] | AGGCAGAGGTGAAAAAGTTG | 1819–1838 | DNA PS | 5 |
| HBV72[a] | AGGCAGAGGTGA | 1827–1838 | DNA PS | 6 |
| HBV43[a] | AGAGATGATTAGGCAGAGGT | 1829–1848 | DNA PS | 7 |
| HBV43M[a] | AGAGAUGAUUAGGCAGAGGT | 1829–1848 | 2'-OME PS/DNA PS | 7 |
| HBV88[b] | GACATGAACAAGAGATGATTAGGCAGAGGT | 1829–1858 | DNA PS | 8 |
| HBV88M[b] | GACAUGAACAAGAGAUGAUUAGGCAGAGGT | 1829–1858 | 2'-OME PS/DNA PS | 8 |
| HBV46[c] | GACATGTACAAGAGATGATT | 1839–1858 | DNA PS | 9 |
| HBV46Y[b] | GACATGAACAAGAGATGATT | 1839–1858 | DNA PS | 9 |
| HBV46MY[b] | GACAUGAACAAGAGAUGAUU | 1839–1858 | 2'-OMe PS | 9 |
| HBV1[b] | GTAGGACATGAACAAGAGAT | 1843–1862 | DNA PS | 10 |
| HBV2[b] | TTGGAGGCTTGAACAGTAGG | 1858–1877 | DNA PS | 11 |
| HBV5[a] | CACAGCTTGGAGGCTTGAAC | 1864–1883 | DNA PS | 12 |
| HBV3[a] | AGCCACCCAAGGCACAGCTT | 1876–1895 | DNA PS | 13 |
| HBV4[b] | TCGATGTCCATGCCCCAAAG | 1894–1913 | DNA PS | 14 |
| HBV92[b] | TAAGGGTCGATGTCCATGCC | 1900–1919 | DNA PS | 15 |
| HBV92M[b] | TAAGGGTCGAUGUCCAUGCC | 1900–1919 | 2'-OMe PS/DNA PS | 15 |
| HBV92M2[b] | TAAGGGUCGAUGUCCATGCC | 1900–1919 | 2'-OMe PS/DNA PS | 15 |
| HBV101[b] | TTATAAGGGTCGATGTCCAT | 1903–1922 | DNA PS | 16 |
| HBV101M[b] | TTATAAGGGTCGAUGUCCAU | 1903–1922 | 2'-OMe PS/DNA PS | 16 |
| HBV94[b] | AAATTCTTTATAAGGGTCGATGTCCAT | 1903–1929 | DNA PS | 17 |
| HBV71[b] | TATAAGGGTCGA | 1910–1921 | DNA PS | 18 |
| HBV93[b] | AAATTCTTTATAAGGGTCGA | 1910–1929 | DNA PS | 19 |

TABLE 1-continued

| OLIGO | Sequence (5' → 3') | Position | Chemistry | SEQ ID NO: |
|---|---|---|---|---|
| HBV93M[b] | AAATTCTTTATAAGGGUCGA | 1910–1929 | 2'-OMe PS/DNA PS | 19 |
| HBV61[b] | GTATCTAGAAGATCTCGTAC | 1981–2000 | DNA PS | 20 |
| HBV60[c] | GCGGTGTCTAGAAGATCTCG | 1984–2003 | DNA PS | 21 |
| HBV60Y[b] | GCGGTATCTAGAAGATCTCG | 1984–2003 | DNA PS | 21 |
| HBV57[c] | GAGGCGGTGTCTAGGAGATC | 1987–2006 | DNA PS | 22 |
| HBV57Y[b] | GAGGCGGTATCTAGAAGATC | 1987–2006 | DNA PS | 22 |
| HBV42[c] | GAGCTGAGGCGGTGTCTAGG | 1992–2011 | DNA PS | 23 |
| HBV42Y[b] | GAGCTGAGGCGGTATCTAGA | 1992–2011 | DNA PS | 23 |
| HBV54[b] | ATACAGAGCTGAGGCGGTAT | 1997–2016 | DNA PS | 24 |
| HBV55[b] | TCCCGATACAGAGCTGAGGC | 2002–2021 | DNA PS | 25 |
| HBV56[b] | AGGCTTCCCGATACAGAGCT | 2007–2026 | DNA PS | 26 |
| HBV53[b] | ACAATGCTCAGGAGACTCTA | 2027–2046 | DNA PS | 27 |
| HBV41[c] | GCAGTATGGTGAGGTGAGCA | 2044–2063 | DNA PS | 28 |
| HBV41Y[b] | GCAGTATGGTGAGGTGAACA | 2044–2063 | DNA PS | 28 |
| HBV51[a] | GAGTGCAGTATGGTGAGGTG | 2048–2067 | DNA PS | 29 |
| HBV50[a] | TGCCTGAGTGCAGTATGGTG | 2053–2072 | DNA PS | 30 |
| HBV52[b] | TTGCTTGCCTGAGTGCAGTA | 2058–2077 | DNA PS | 31 |
| HBVpol-1 | GGCATTTGGTGGTCTATAAG | 2294–2314 | DNA PS | 42 |
| HBVpol-2 | GATAGGGGCATTTGGTGGTC | 2300–2319 | DNA PS | 43 |
| HBVpol-3 | TGTTGATAGGATAGGGGCAT | 2309–2328 | DNA PS | 44 |
| HBV6 | ACCCAAGGCACAGCTTGGAG | 1872–1891 | DNA PS | 45 |
| HBVpol-A[b] | GAcAGGGGCATTTGGTGGTC | 2300–2319 | DNA PS | 46 |
| HBVpol-B[b] | GATAGGGGCCTTTGGTGGTC | 2300–2319 | DNA PS | 47 |
| HBVpol-C[b] | GATAGGGGCATTTGGTGCTC | 2300–2319 | DNA PS | 48 |
| HBVpol-D[b] | GAcAGGGGCCTTTGGTGCTC | 2300–2319 | DNA PS | 49 |
| HBV69 | TAAGGGTCGA | 1910–1919 | DNA PS | 53 |
| HBV73 | AGGCAGAGGT | 1829–1838 | DNA PS | 54 |

[a]target strain = ayw and adw
[b]target strain = ayw
[c]target strain = adw
underscoring == 2'-OMe RNA PS
N = PS DNA
lower case letters indicate mismatched nucleotides Sequence positions listed in Table 1 represent the standard orientation as shown by Raney et al. in *Molecular Biology of the Hepatitis B Virus* (McLachlan, ed. (1991): CRC Press, Boca Raton, Fla. Ch 1, pp 2–37). Synthetic "noncontiguous" oligonucleotides of the invention target noncontiguous portions of the epsilon region, and within this region, bind across the base of the stem loop and from the base to within the stem.

Representative noncontiguous oligonucleotides of the invention are set forth below in Table 2.

TABLE 2

| Oligo | Sequence (5' → 3') | Site 1 (5') | Site 2 (3') | SEQ ID NO: |
|---|---|---|---|---|
| HBV-19[b] | TAAGGGTCGAAGAGATGATT | 1839–1848 | 1910–1919 | 32 |
| HBV-64[b] | AGAGATGATTTAAGGGTCGA | 1839–1848 | 1910–1919 | 33 |
| HBV-64M1[b] | AGAGATGATTUAAGGGUCGA | 1839–1848 | 1910–1919 | 33 |
| HBV-64M2[b] | AGAGATGATTTAAGGGUCGA | 1839–1848 | 1910–1919 | 33 |
| HBV-68[b] | TAAGGGTCGAAGGCAGAGGT | 1829–1838 | 1910–1919 | 34 |
| HBV-66[b] | AGGCAGAGGTTAAGGGTCGA | 1829–1838 | 1910–1919 | 35 |
| HBV-79[b] | TATAAGGGTCGAAGGCAGAGGTGA | 1827–1838 | 1910–1921 | 36 |
| HBV-67[b] | AGGCAGAGGTGATATAAGGGTCGA | 1827–1838 | 1910–1921 | 37 |
| HBV-67M1[b] | AGGCAGAGGTGAUAUAAGGGUCGA | 1827–1838 | 1910–1921 | 37 |
| HBV-67M2[b] | AGGCAGAGGUGATATAAGGGTCGA | 1827–1838 | 1910–1921 | 37 |
| HBV-87[b] | AGAGATGATTAGGCAGAGGTTAAGGGTCGA | 1829–1848 | 1910–1921 | 38 |
| HBV-87M[b] | AGAGAUGAUUAGGCAGAGGTTAAGGGTCGA | 1829–1848 | 1910–1921 | 38 |
| HBV-89[b] | GACATGAACAAGAGATGATTTAAGGGTCGA | 1839–1858 | 1910–1921 | 39 |
| HBV-89M[b] | GACAUGAACAAGAGAUGAUUAAGGGTCGA | 1839–1858 | 1910–1921 | 39 |
| HBV-90[b] | AGAGATGATTTAAGGGTCGATGTCCATGCC | 1839–1848 | 1900–1919 | 40 |
| HBV-90M[b] | AGAGAUGAUUTAAGGGTCGAUGUCCAUGCC | 1839–1848 | 1900–1919 | 40 |
| HBV-91[b] | AGGCAGAGGTTAAGGGTCGATGTCCATGCC | 1829–1848 | 1900–1919 | 41 |
| HBV-91M[b] | AGGCAGAGGTTAAGGGTCGAUGUCCAUGCC | 1829–1848 | 1900–1919 | 41 |

[a]target strain = ayw and adw
[b]target strain = ayw
[c]target strain = adw
underscoring = 2'-OMe RNA PS
N = PS DNA Synthetic oligonucleotides of the invention specific for HBV nucleic acid are composed of deoxyribonucleotides, ribonucleotides, 2'-O-methyl-ribonucleotides, or any combination thereof, with the 5' end of one nucleotide and the 3' end of another nucleotide being covalently linked. These oligonucleotides are at least 6 nucleotides in length, but are preferably 12 to 50 nucleotides long, with 20 to 30 mers being the most common.

These oligonucleotides can be prepared by art recognized methods. For example, nucleotides can be covalently linked using art recognized techniques such as phosphoramidite, H-phosphonate chemistry, or methylphosphoramidite chemistry (see, e.g., Goodchild (1990) *Bioconjugate Chem.* 2:165–187; Uhlmann et al. (1990) *Chem. Rev.* 90:543–584; Caruthers et al. (1987) *Meth. Enzymol.* 154:287–313; U.S. Pat. No. 5,149,798) which can be carried out manually or by an automated synthesizer and then processed (reviewed in Agrawal et al. (1992) *Trends Biotechnol.* 10:152–158).

The oligonucleotides of the invention may also be modified in a number of ways without compromising their ability to hybridize to HBV nucleic acid. For example, the oligonucleotides may contain other than phosphodiester internucleotide linkages between the 5' end of one nucleotide and the 3' end of another nucleotide in which the 5' nucleotide phosphate has been replaced with any number of chemical groups, such as a phosphorothioate. Oligonucleotides with phosphorothioate linkages can be prepared using methods well known in the field such as phosphoramidite (see, e.g., Agrawal et al. (1988) *Proc. Natl. Acad. Sci.* (USA) 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used. Examples of other chemical groups include alkylphosphonates, phosphorodithioates, alkylphosphonothioates, phosphoramidates, 2'-O-methyls, carbamates, acetamidate, carboxymethyl esters, carbonates, and phosphate triesters. Oligonucleotides with modified internucleotide linkages can be prepared according to known methods (see, e.g., Goodchild (1990) *Bioconjugate Chem.* 2:165–187; Agrawal et al. (*Proc. Natl. Acad. Sci.* (USA) (1988) 85:7079–7083); Uhlmann et al. (*Chem. Rev.* (1990) 90:534–583; and Agrawal et al. (*Trends Biotechnol.* (1992) 10:152–158)).

Other modifications include those which are internal or are at the end(s) of the oligonucleotide molecule and include additions to the molecule at the internucleoside phosphate linkages, such as cholesteryl or diamine compounds with varying numbers of carbon residues between the two amino groups, and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5'-substituted oligonucleotide having a sugar which, at one or both its 3' and 5' positions is attached to a chemical group other than a hydroxyl or phosphate group (at its 3' or 5' position). Other modified oligonucleotides are capped with a nuclease resistance-conferring bulky substituent at their 3' and/or 5' end(s), or have a substitution in one or both nonbridging oxygens per nucleotide. Such modifications can be at some or all of the internucleoside linkages, as well as at either or both ends of the oligonucleotide and/or in the interior of the molecule (reviewed in Agrawal et al. (1992) *Trends Biotechnol.* 10:152–158).

To determine whether an oligonucleotide of the invention is capable of successfully hybridizing to its target, an RNase H assay was performed (Frank et al. (1993) *Proc. Int. Conf. Nucleic Acid Med. Applns.* 1:4.14 (abstract)). This assay is useful when a region of at least four contiguous nucleotides of the oligonucleotide is DNA and the target is RNA. Hybridization of the DNA portion of the oligonucleotide to the RNA target is identified by cleavage at that site by RNase H.

Figure 2:
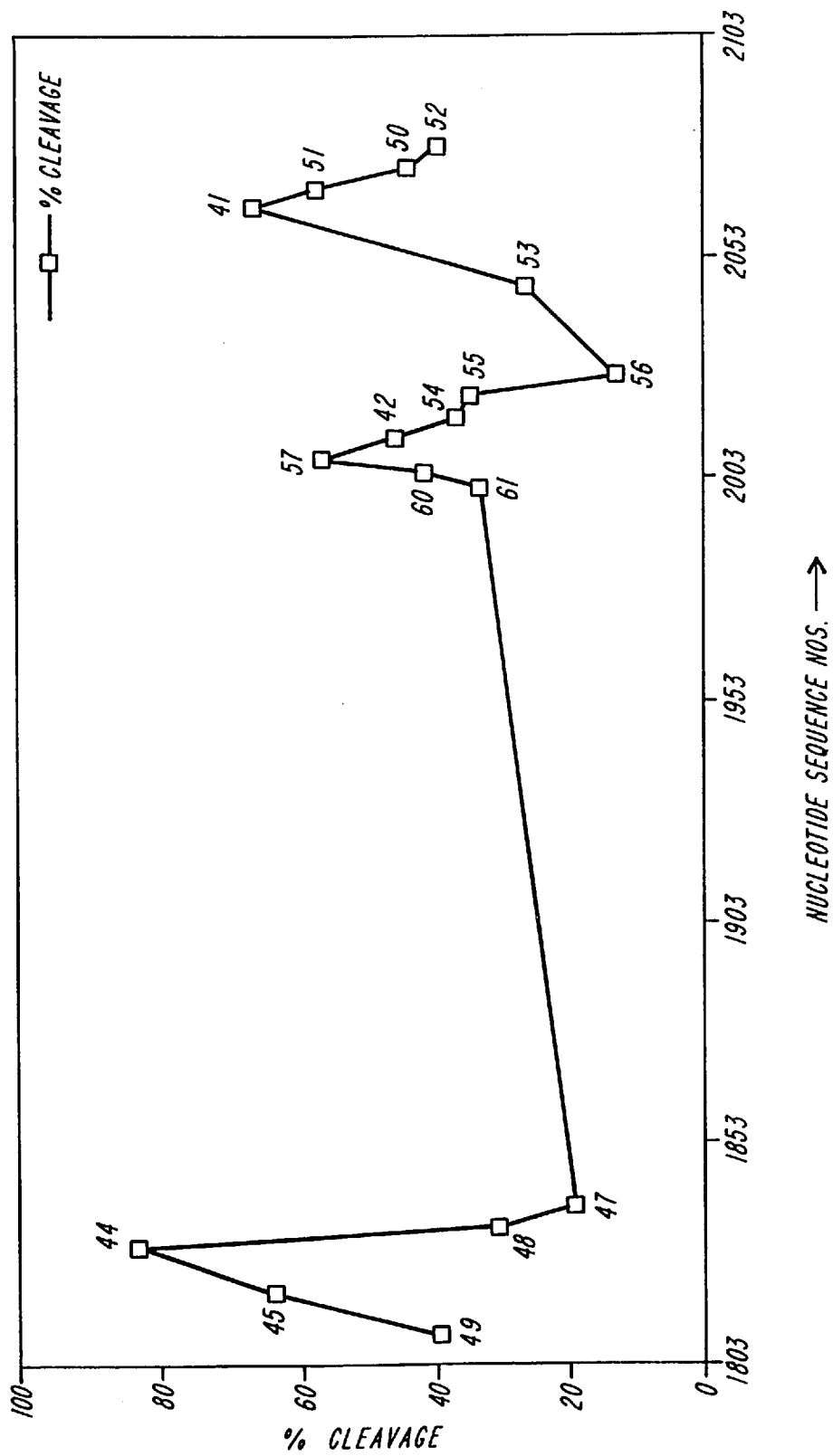
FIG. 2 is a graphic representation showing sites on HBV RNA accessible to oligonucleotide hybridization detected by RNase H cleavage wherein the numbers represent specific HBV oligonucleotides of the invention.

In vitro transcribed HBV RNA (adw strain) was probed for sites accessible to oligonucleotide hybridization using a randomized library of 20 base oligodeoxynucleotides (approximately $4^{20}$ sequences). Hybridization to the RNA was detected by RNase H cleavage of the end-labelled transcript. Three regions were identified by this assay. One region was in the 5' untranslated region, between 113 and 70 bases upstream from the core initiator, and two regions were in the coding regionfor core, between 78 and 174 bases downstream from the core initiator. Contiguous oligodeoxynucleotide phosphorothioates were prepared against these regions and their ability to activate RNase H cleavage of the transcript measured. The results shown in FIG. 2 demonstrate single peaks of activity in each region, corresponding to nt 1809–1828 (HBV44, SEQ ID NO:3) in the 5' untranslated region, and nt 1987–2006 (HBV57, SEQ ID NO:22) and nt 2044–2063 (HBV41, SEQ ID NO:28) in the coding region for core.

Figure 3:
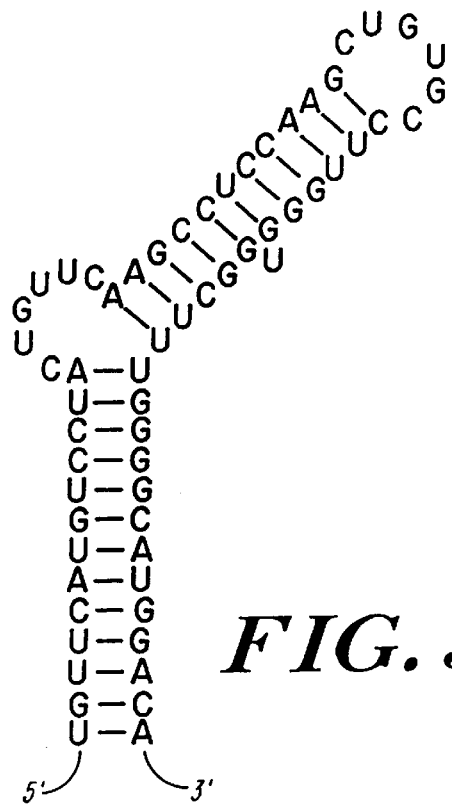
FIG. 3 is a schematic representation showing the sequence and two-dimensional structure of the epsilon region.
Figure 4A:
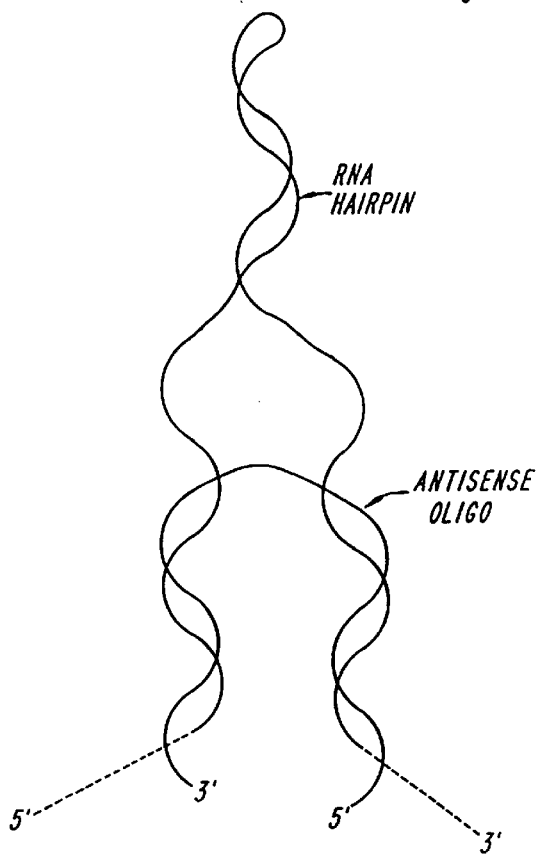
FIG. 4A is a diagrammatic representation showing mode A of oligonucleotide binding to the base of DNA and RNA stems.
Figure 4B:
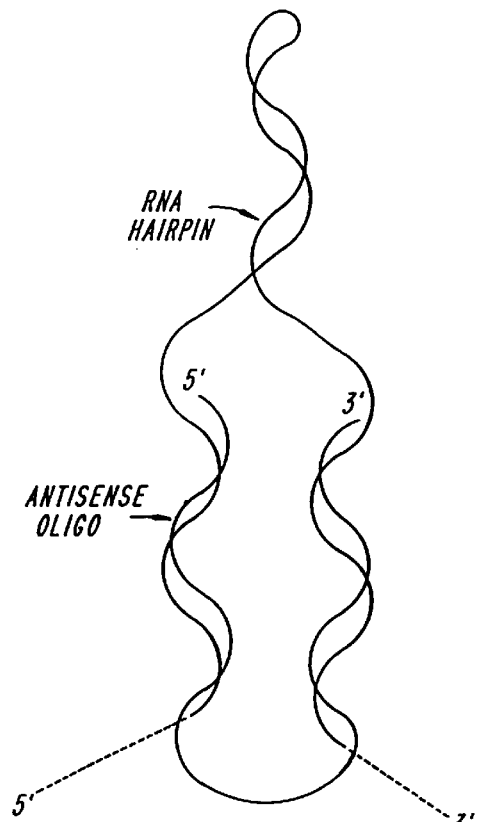
FIG. 4B is a diagrammatic representation showing mode B of oligonucleotide binding to the base of DNA and RNA stems.

Noncontiguous oligonucleotides targeted to the HBV epsilon region have also been prepared and tested. The epsilon region is characterized by an RNA stem-loop structure consisting primarily of double-stranded RNA with a single-stranded bulge and loop of 6 bases each (FIG. 3). Two modes of hybridization of these oligonucleotides have been discovered and are shown in FIGS. 4A and 4B. Mode B in FIG. 4B appears to be preferred as demonstrated by the cleavage of the RNA by ribonuclease H on both sides of the stem. The ability of RNase H to cleave an RNA in this manner inflicts greater damage on the RNA than normal antisense oligodeoxynucleotides, while allowing the targeting of a biologically important region that is otherwise difficult to target due to its double-stranded nature.

Semirandom oligonucleotides consist of a defined sequence of 2'-O-methyl ribonucleotides and an undefined tail synthesized as a mixture of all four deoxyribonucleosides at each position. The 2'-O-methyl portion serves as a sequence-specific anchor, unable to activate RNase H. The random DNA sequence can be on the 3' or 5' side of the defined 2'-O-methyl sequence allowing for hybridization to nearby sequences. Hybridization of the DNA portion to RNA is identified by cleavage at that site by RNase H.

The RNase H cleavage assay was used to test the ability of oligonucleotides to bind across the base of the well characterized RNA hairpin structure found in the epsilon region of HBV pregenomic and messenger RNA (FIG. 3). It was expected that a semirandom oligonucleotide targeted to the sequence 5' of the epsilon stem might target the sequence 3' of the stem when the random DNA sequence was on the 5' end of the oligonucleotide, as shown in FIG. 4A, mode A.

Surprisingly, the experiments showed that cleavage was seen on the 3' side of the epsilon region only when the random portion of the oligonucleotide was on the 3' end, hybridizing as shown in FIG. 4B, mode B. The converse was also true. When the 2'-O-methyl portion was targeted to the sequence on the 3' side of epsilon, cleavage was seen on the 5' side only with the random DNA sequence on the 5' side of the semirandomer.

Based on this information, several oligodeoxynucleotide phosphorothioates were prepared to test the hypothesis that hybridization by mode B is preferred when spanning the base of an RNA stem. 20 mer and 24 mer noncontiguous oligonucleotides (Table 2) were prepared as well as the 10 mers and 12 mers corresponding to the "arms" of the noncontiguous sequences.

Figures 6A, 6B:
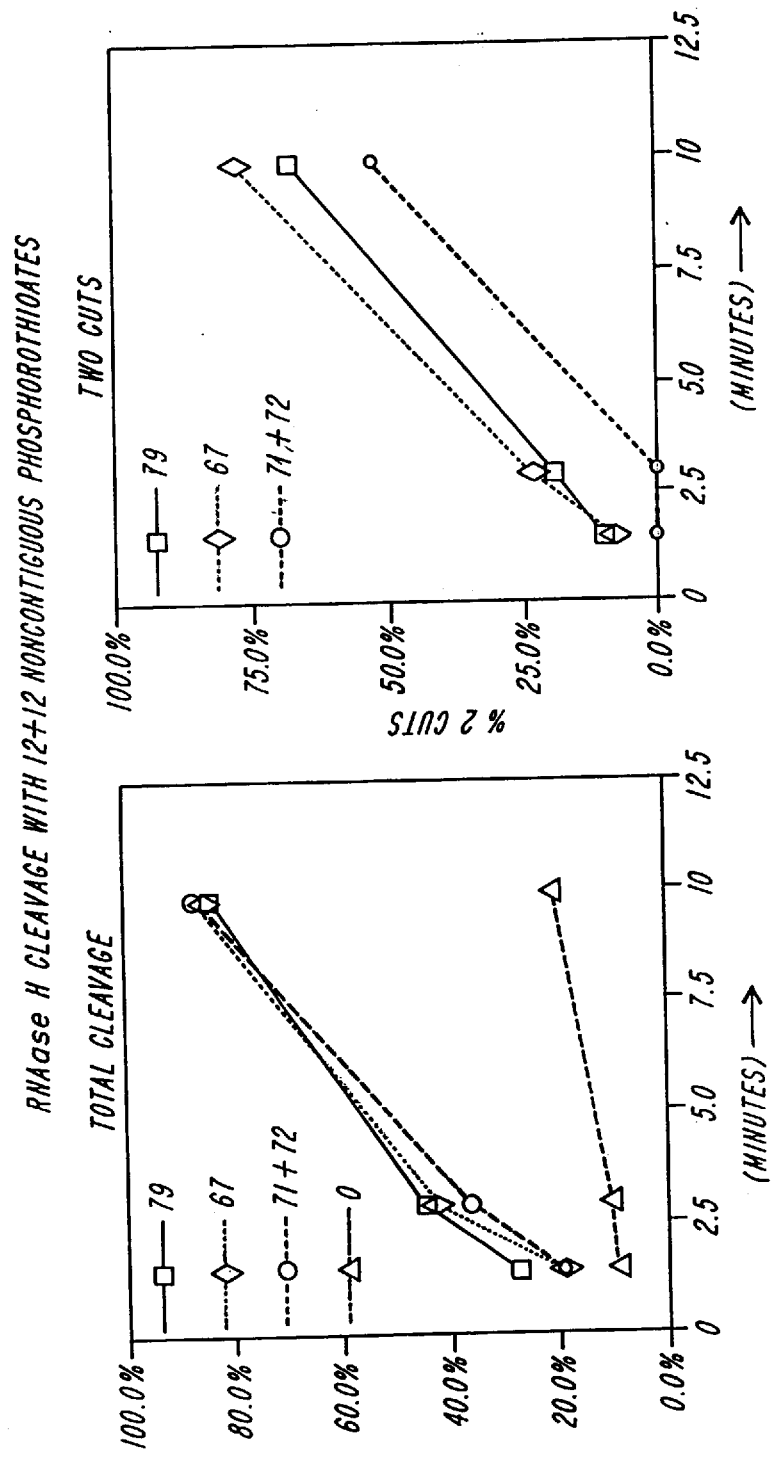
FIG. 6A is a graphic representation showing the results of RNase H cleavage in the presence of noncontiguous oligonucleotides having 12 nucleotides complementary to the 5' side (site 1) of the epsilon region and 12 nucleotides complementary to the 3' side of the epsilon region (12+12)
FIG. 6B is a graphic representation showing the results of RNase H cleavage with 12+12 noncontiguous oligonucleotides (two cuts)

The ability of these oligonucleotides to activate cleavage of internally $^{32}$P-labelled HBV precore-core RNA was tested in the presence of RNase H. FIG. 5A shows total RNA cleavage with 10+10 noncontiguous oligodeoxynucleotide phosphorothioates (ten nucleotides at the 5' end targeting 3' of the RNA stem and the next ten nucleotides at the 3' end targeting 5' of the RNA stem). Both noncontiguous oligonucleotides, HBV66 (SEQ ID NO:35) and HBV68 (SEQ ID NO:34), activate RNase H cleavage of the transcript more effectively than the mixture of 10 mer arms, HBV69 (SEQ ID NO:53) and HBV73 (SEQ ID NO:54). For the 12+12 oligonucleotides (FIGS. 6A and 6B), RNA cleavage activated by the mixture of 12 mer arms, HBV71 (SEQ ID NO:18) and HBV72 (SEQ ID NO:6), is equal to the RNA cleavage in the presence of the noncontiguous oligodeoxynucleotide phosphorothioates (HBV79, SEQ ID NO:3G and HBV67 (SEQ ID NO:37) (FIG. 6A).

If a single oligodeoxynucleotide were able to bind across the base of epsilon to sequences on either side of the stem, RNase H might cleave both sites and effectively cut out the epsilon stem-loop from the RNA. The results of double cleavage of HBV precore-core RNA labelled internally with [α-$^{32}$P] dCTP are shown in FIGS. 5B and 6B. The efficiency of production of the twice cleaved product by RNase H in the presence of HBV66 (the noncontiguous 10+10 oligonucleotide hybridizing by mode B) was greater after 10 minutes than in the presence of HBV68 (the 10+10 noncontiguous oligonucleotide hybridizing by mode A) (FIG. 5B). The mixture of the individual 10 mer arms was unable to activate cleavage on both sides of the same stem-loop (HBV69+HBV73) (FIG. 5B). The 12+12 noncontiguous phosphorothioates show the same ability to bind across the base of the RNA stem. As shown in FIG. 6B, HBV79 (SEQ ID NO:36) and HBV67 (SEQ ID NO:37) efficiently activate RNase H cleavage on both sides of the stem after only 1.5 minutes, with hybridization by mode B (HBV67) showing slightly more cleavage than mode A (HBV79). Double cleavage of the transcript in the presence of the mixture of 12 mer arms (HBV71+HBV72) was much slower (FIG. 6B).

When oligonucleotides hybridizing via mode B were lengthened to allow strand invasion of the RNA stem, disruption of the stem-loop structure occurred. Oligonucleotides HBV89 (SEQ ID NO:39), HBV90 (SEQ ID NO:40), and HBV91 (SEQ ID NO:41) bind across the base of epsilon via mode B and strand invade on either the 5' side (HBV89) or the 3' side (HBV90 and HBV91) of the RNA stem. HBV89M is an extension of HBV64M with ten 2'-O-methyl RNA residues invading the RNA stem on the 5'-side. Addition of these strand invading nucleotides increased the cleavage efficiency from 23% to 32% at 100 nM oligonucleotide. HBV90 and HBV91 PS were also able to strand invade as evidenced by RNase H cleavage within the stem near the core initiator.

Figure 7:
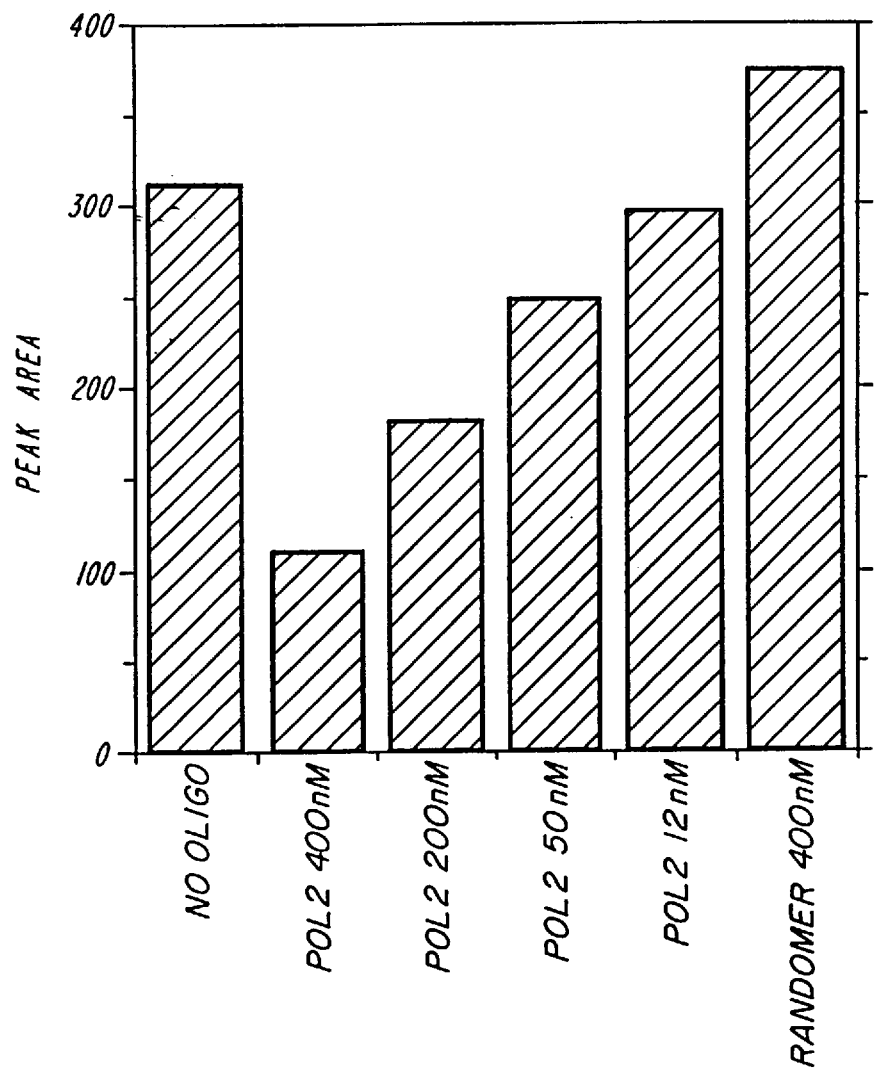
FIG. 7 is a graphic representation showing the inhibitory effect of different concentrations of HBVpol-2 on the translation of HBVpol RNA, wherein peak areas are arbitrary units.

The oligonucleotides of the invention can be assayed for antisense inhibitory activity with a number of different assays. For example, an in vitro translation assay can be used to test antisense activity in which an antisense oligonucleotide can inhibit synthesis of a protein product encoded by the targeted mRNA. In such an assay, oligonucleotides targeted to the polymerase gene were tested against both target and an unrelated control RNA in the wheat germ translation system. In this assay, the contiguous oligonucleotide HBVpol-2 (SEQ ID NO:43) at 400 nM showed good specific activity causing between 70% and 100% translation inhibition. Results are represented graphically in FIG. 7.

Figure 8:
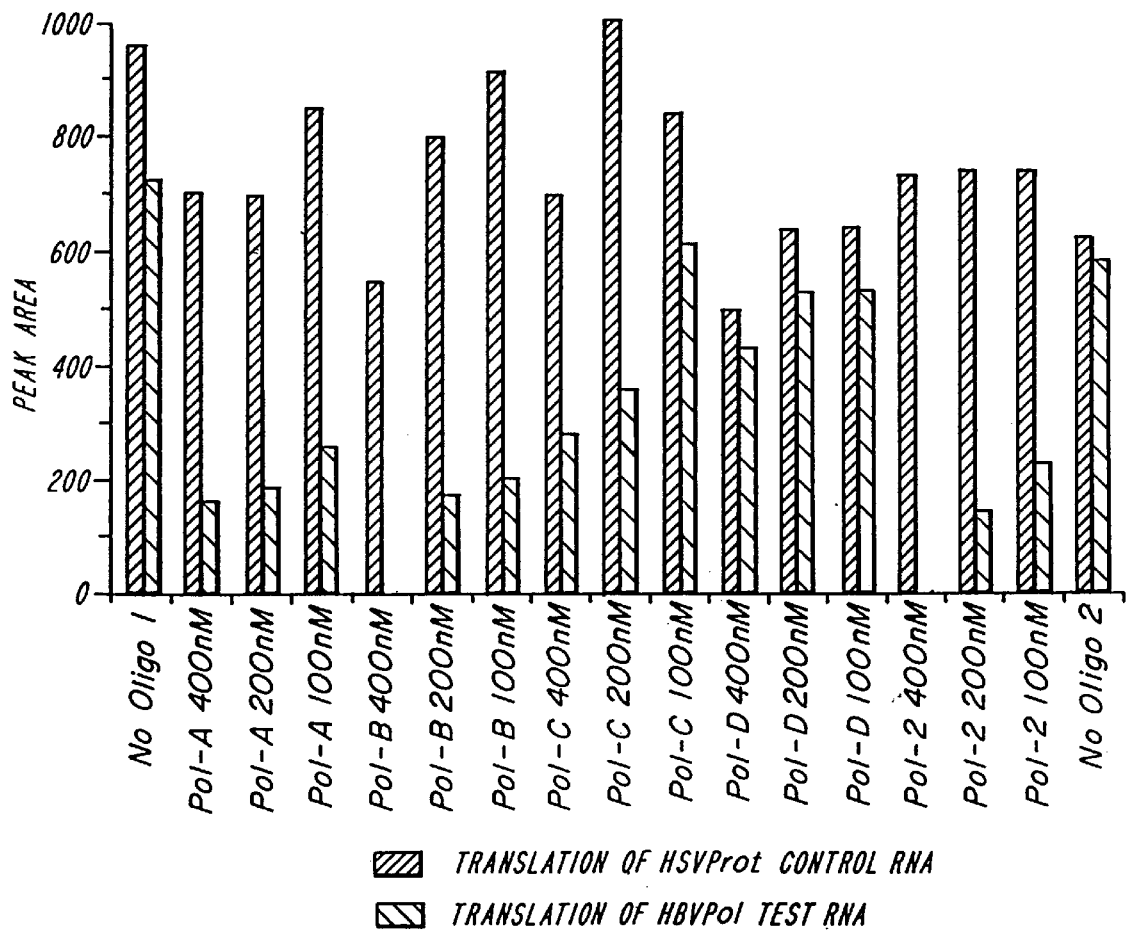
FIG. 8 is a graphic representation showing the inhibitory effect of different concentrations of HBVpol-2 and related mismatched oligonucleotides, HBVpol-A, HBVpol-B, HBVpol-C, and HBVpol-D, on the translation of HBVpol RNA, wherein the dark bars represent translation of control RNA, and the hatched bars represent translation of HBVpol test RNA, wherein peak areas are arbitrary units.

This assay was also used to compare the activity of mismatched oligonucleotides to the activity of the parent oligonucleotide. Four such oligonucleotides, all derivatives of HBVpol-2 (HBVpol-A, SEQ ID NO:46; HBVpol-B, SEQ ID NO:47; HBVpol-C, SEQ ID NO:48, HBVpol-D, SEQ ID NO:49) (Table 1) were synthesized and tested in the assay. The results are shown in FIG. 8. Those oligonucleotides with a single mismatch (SEQ ID NO:46–48) showed varying degrees of reduction in activity when compared to HBVpol-2 (SEQ ID NO:43). Three mismatches in the oligonucleotide (see SEQ ID NO:49) abrogated antisense activity.

Oligonucleotides targeted to the polymerase translation initiation region were also tested in mammalian cells using a firefly luciferase reporter gene assay. The 35 nucleotide region spanning the translation start site of the HBV ayw polymerase gene from nt 2294–2328 was cloned 5' to, and in frame with, the entire open reading frame of the firefly luciferase gene in the plasmid pGLori, to produce the plasmid pGLpol (FIG. 10). Transcription of this pol-luciferase gene fusion was placed under the control of the cytomegalovirus early gene promoter. Expression of the pol-luciferase fusion in mammalian cells was quantified in a luminometer by addition of luciferin substrate and ATP cofactor to cell lysates. In all cellular antisense assays, a random sequence 20 mer phosphorothioate oligonucleotide (random 20 mer PS) was used as a negative control. In addition, a 20 mer phosphorothioate antisense oligonucleotide targeting the first 20 nucleotides of the coding region of the firefly luciferase gene was used as a positive control (Luc+1–+20; SEQ ID NO:50). This target is retained in both pol fusion and control luciferase constructs. The reduction in luciferase levels in cells treated with antisense oligonucleotides compared to luciferase levels in cells treated with a negative control random oligonucleotide is a measure of the sequence specific activity of the antisense oligonucleotides.

Figure 9:
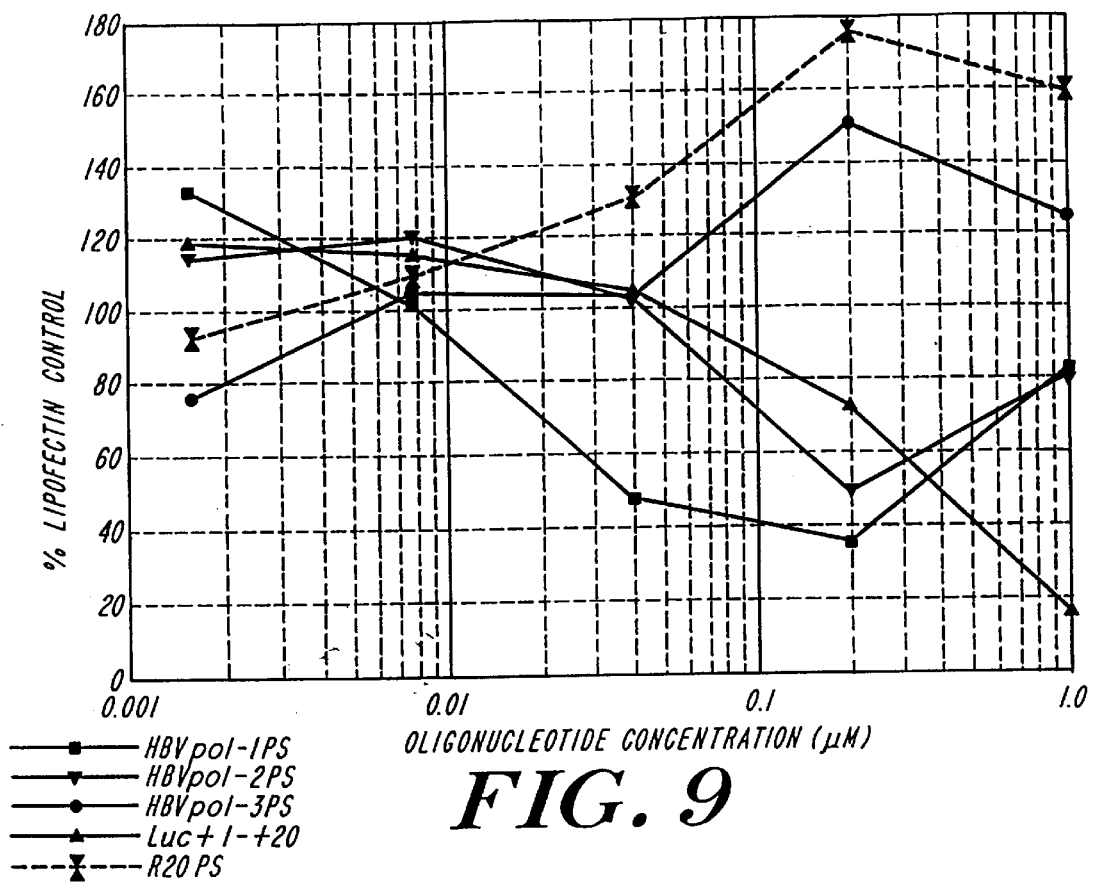
FIG. 9 is a graphic representation showing the inhibitory effect of contiguous oligonucleotides of the invention (HBVpol-1, HBVpol-2, and HBVpol-3) on luciferase expression.

Oligonucleotides of the invention were tested against the HBV subtype ayw polymerase gene-luciferase fusion construct in stably transfected HepG2 cells. The results are shown in FIG. 9. HBVpol-1 (SEQ ID NO:42) and HBVpol-2 (SEQ ID NO:43) had sequence-specific antisense activity. None of these PS oligonucleotides, with the exception of the positive control Luc+1–+20 oligonucleotide, exhibited antisense activity in HepG2 cells stably transfected with the parent pGLori sequence.

In addition to the HBVpol-luciferase fusion construct, three different HBV-luciferase fusion constructs were generated incorporating the region around the HBV subtype ayw epsilon region (FIG. 10). The pGLE construct consists of 71 nucleotides representing the epsilon stem loop region (nt 1843–1913), inserted between the cytomegalovirus immediate early gene promoter and luciferase reporter gene in the plasmid pGLori. Translation in this construct should initiate at the HBV core gene initiation site (nt 1903).

The constructs pGLE2 and pGLE3 (FIG. 10) consist of 130 nucleotides representing the precore translation start site and epsilon stem loop region (nt 1813–1943) inserted between the cytomegalovirus immediate early gene promoter and luciferase reporter gene in the plasmid pGLori. In these two constructs the translation start site of the luciferase gene was removed. In addition, the HBV core gene translation start site was mutated in pGLE3 (nt 1904: T→C). A complementary mutation was introduced at nt 1854 (A→G) to maintain the base pairing in the epsilon stem. In pGLE2 translation can be initiated from the precore or core translation start site. In pGLE3 translation can only be initiated at the precore translation start site.

Figure 11:
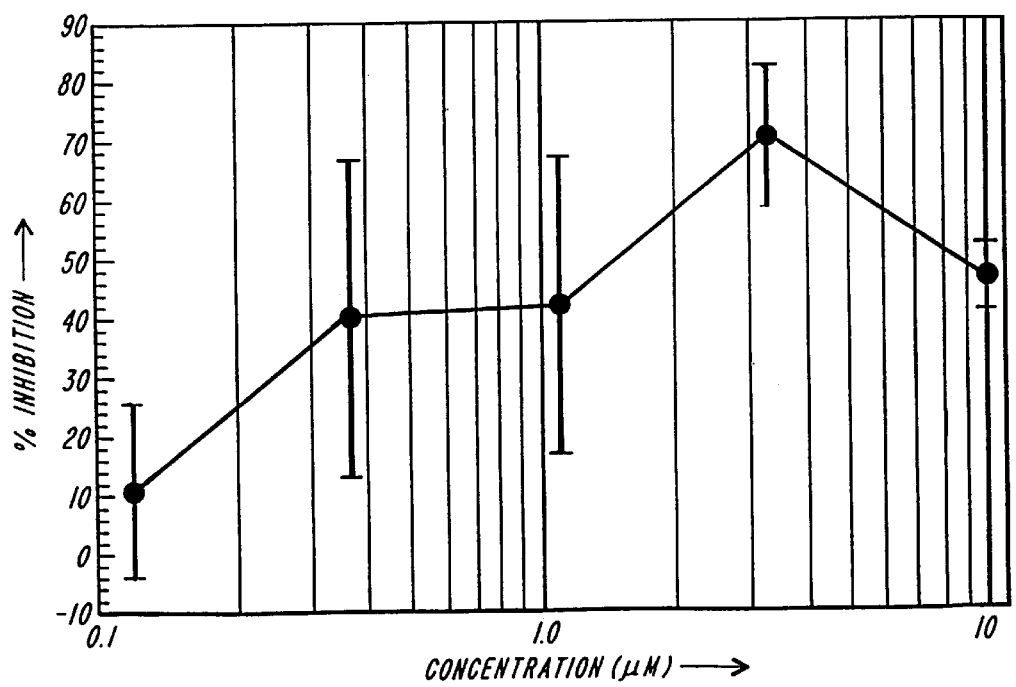
FIG. 11 is a graphic representation showing the results of a Southern hybridization assay demonstrating inhibition of the formation of replicative intermediate (RI) HBV DNA in HepG2.2.15 cells in the presence of different concentrations of HBV6.
Figure 12:
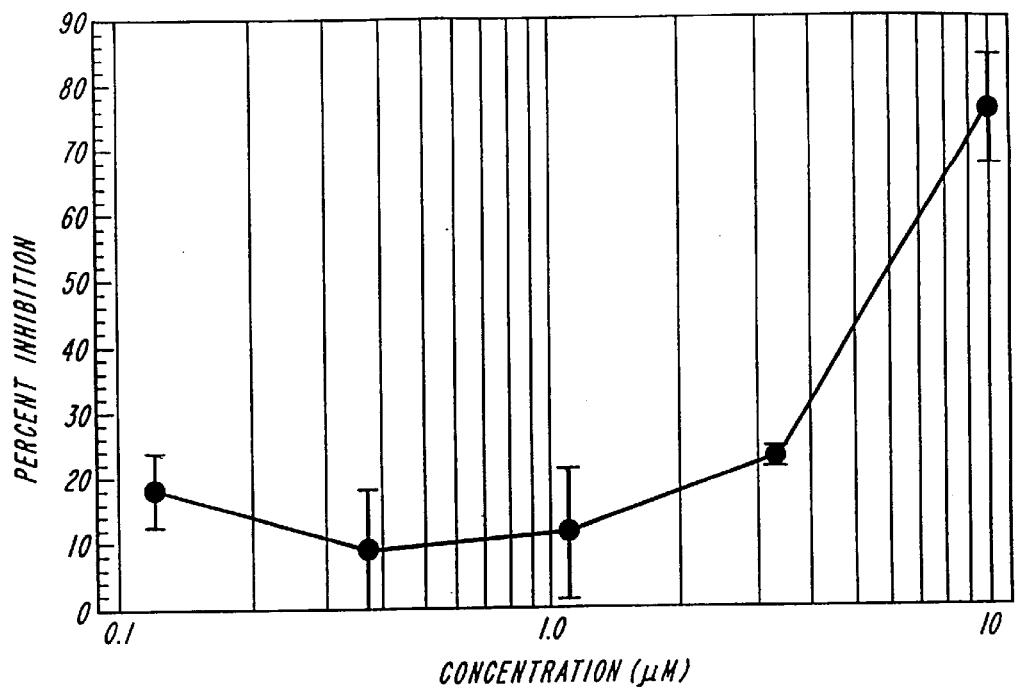
FIG. 12 is a graphic representation showing the results of a Southern hybridization assay demonstrating inhibition of the formation of replicative intermediate (RI) HBV DNA in HepG2.2.15 cells in the presence of different concentrations of HBV67.

The activity of antisense oligonucleotides was also studied in a viral assay in HepG2.2.15 cells, which have been stably transfected with plasmids carrying whole HBV genomes (Sells et al. (1987) *Proc. Nat. Acad. Sci.* 84:1005–1009; Sureau et al. (1986) Cell 47:37–47). While a number of assays for HBV inhibitors based on the HepG2 2.2.15 cell line have been reported (Jansen et al. (1993) *Antimicrob. Agent. Chemother.* 37:441–447; Korba et al. (1992) *Antiviral Res.* 19:55–70), these involve the detection of HBV DNA by means of dot blot or PCR, tests which do not provide data concerning the precise source of the measured DNA. A more definitive test is Southern hybridization, which provides data concerning the character of the detected DNA in addition to quantitation. This assay has been described previously for the screening of anti-HBV compounds on HepG2.2.15 cells (Doong et al. (1991) *Proc. Nat. Acad. Sci.* (USA) 88:8495–8499). In view of the many potential sources of HBV DNA from transfected cells, this assay allows for a more meaningful interpretation of results than the other methods mentioned. When HBV6 (SEQ. ID NO:45) was titrated, significant inhibition was found (FIG. 11). Inhibition was also found to be mediated by the stem-loop bridging oligonucleotide, HBV67 (SEQ. ID NO:37) (FIG. 12).

In addition to Southern hybridizations, kinetic PCR was performed to assay the supernatants from the HepG2.2.15 cells. This procedure was carried out as described by Higuchi et al. (*Biotechnol.* (1993) 11:1026–1030). All PCRs were carried out with two sets of external controls which consisted of a dilution series of a known concentration of plasmid DNA that contained the HBV core gene amplified with the same primer set. These controls generated a standard curve that was used to calculate the copy number of HBV genomes in the supernatants from cells exposed to the various dilutions of compound. From these data, $IC_{50}$ values were calculated for each compound and are shown below in Table 3.

TABLE 3

| SEQ ID NO: | Oligo | $IC_{50}$ ($\mu M$) |
|---|---|---|
| 3 | HBV44 | 0.7 |
| 4 | HBV48 | 0.7 |
| 18 | HBV4 | 1.2 |
| 42 | HBVpol-2 | 3.7 |
|  | Randomer | 4.5 |

The results of this experiment demonstrate that the HBV-specific oligonucleotides of the invention have inhibitory activity.

The synthetic antisense oligonucleotides of the invention may be in the form of a therapeutic composition or formulation useful in inhibiting HBV replication in a cell, and in treating hepatitis B infections and associated conditions in an animal, such as acute and chronic hepatitis and hepatocellular carcinoma. They may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of HBV expression. For example, combinations of synthetic oligonucleotides, each of which is directed to different regions of the HBV nucleic acid, may be used in the pharmaceutical compositions of the invention. The pharmaceutical composition of the invention may further contain other chemotherapeutic drugs for the treatment of hepatocellular carcinoma. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-HBV or anti-cancer factor and/or agent to minimize side effects of the anti-HBV factor and/or agent.

The pharmaceutical composition of the invention may be in the form of a liposome in which the synthetic oligonucleotides of the invention are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235, 871; 4,501,728; 4,837,028; and 4,737,323. The pharmaceutical composition of the invention may further include other lipid carriers, such as Lipofectamine, or cyclodextrins (Zhao et al. (1995) *Antisense Res. Dev.* (in press)) and the like which enhance delivery of oligonucleotides into cells, or such as slow release polymers.

As used herein, the term "therapeutically effective amount" means the total amount of each active component of the pharmaceutical composition or method that is sufficient to show a meaningful patient benefit, i.e., a reduction in pain associated with acute or chronic hepatitis or the remission of hepatocellular carcinoma. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one or more of the synthetic oligonucleotides of the invention is administered to a subject afflicted with an HBV-associated disease. The synthetic oligonucleotide of the invention may be administered in accordance with the method of the invention either alone or in combination with other known therapies for the HBV-associated disease. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

It may be desirable at times to use a mixture of different oligonucleotides targeting different conserved sites within a given viral genome. Such a mixture of oligonucleotides may be in the form of a therapeutic composition comprising at least one, and preferably two or more oligonucleotides in a single therapeutic composition (i.e., a composition comprising a physical mixture of at least two oligonucleotides). These oligonucleotides may have the same or different sequences. At least one, preferably two or more oligonucleotides may be administered simultaneously or sequentially as a single treatment episode in the form of separate pharmaceutical compositions.

Administration of the synthetic oligonucleotide of the invention used in the pharmaceutical composition or to practice the method of treating an animal can be carried out in a variety of conventional ways, such as oral ingestion, inhalation, or cutaneous, subcutaneous, intramuscular, or intravenous injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, cutaneous or subcutaneous injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patient has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the various pharmaceutical compositions used to practice the method of the present invention should contain about 1.0 ng to about 2.5 mg of synthetic oligonucleotide per kg body weight.

The duration of intravenous therapy using the pharmaceutical composition of the present invention will vary, depending on the severity of the disease being treated and the condition and potential idiosyncratic response of each individual patient. It is contemplated that the duration of each application of the synthetic oligonucleotide will be in the range of 12 to 24 hours of continuous intravenous administration. Ultimately the attending physician will decide on the appropriate duration of intravenous therapy using the pharmaceutical composition of the present invention.

The oligonucleotides of the invention may also be a part of kits for inhibiting HBV replication and infection in a cell. Such a kit includes a synthetic oligonucleotide specific for HBV nucleic acid, such as those described herein. For example, the kit may include at least one of the synthetic contiguous oligonucleotides of the invention, such as, but not limited to, those having SEQ ID NO: 1–31 and 42–48. These oligonucleotides may have modified backbones, such as those described above, and may be RNA/DNA hybrids containing, for example, at least one 2'-O-methyl. The kit of the invention may optionally include buffers, cell or tissue preparation reagents, cell or tissue preparation tools, vials, and the like.

Other kits of the invention are for detecting the presence of HBV in a sample, such as a solution or biological sample, such as a fluid, tissue, tissue homogenate, and the like. These kits contain at least one synthetic oligonucleotide complementary to contiguous or noncontiguous regions of HBV RNA, and means for detecting the oligonucleotide hybridized with the nucleic acid if HBV is present in the sample.

The following examples illustrate the preferred modes of making and practicing the present invention, but are not meant to limit the scope of the invention since alternative methods may be utilized to obtain similar results.

EXAMPLES

1. Oligonucleotide Synthesis

Oligonucleotides were synthesized using standard phosphoramidite chemistry (Beaucage (1993) *Meth. Mol. Biol.* 20:33–61) on either an ABI 394 DNA/RNA synthesizer (Perkin-Elmer, Foster City, Calif.), a Pharmacia Gene Assembler Plus (Pharmacia, Uppsala, Sweden) or a Gene Assembler Special (Pharmacia, Uppsala, Sweden) using the manufacturers' standard protocols and custom methods. The custom methods served to increase the coupling time from 1.5 min to 12 min for the 2'-O-methyl RNA amidites. The Pharmacia synthesizers required additional drying of the amidites, activating reagent and acetonitrile. This was achieved by the addition of 3 Å molecular sieves (EM Science, Gibbstown, N.J.) before installation on the machine.

DNA β-cyanoethyl phosphoramidites were purchased from Cruachem (Glasgow, Scotland). The DNA support was 500 Å pore size controlled pore glass (CPG) (PerSeptive Biosystems, Cambridge, Mass.) derivatized with the appropriate 3' base with a loading of between 30 to 40 mmole per gram. 2'-O-methyl RNA β-cyanoethyl phosphoramidites and CPG supports (500 Å) were purchased from Glen Research (Sterling, Va.). For synthesis of random sequences, the DNA phosphoramidites were mixed by the synthesizer according to the manufacturer's protocol (Pharmacia, Uppsala, Sweden).

All 2'-O-methyl RNA-containing oligonucleotides were synthesized using ethylthiotetrazole (American International Chemical (AIC), Natick, Mass.) as the activating agent, dissolved to 0.25M with low water acetonitrile (Aldrich, Milwaukee, Wis.). Some of the DNA-only syntheses were done using 0.25M ethylthiotetrazole, but most were done using 0.5M 1-H-tetrazole (AIC). The sulfurizing reagent used in all the PS oligonucleotides was 3H-1,2-benzodithiol-3-one 1,1-dioxide (Beaucage Reagent, R.I. Chemical, Orange, Calif., or AIC, Natick, Mass.) as a 2% solution in low water acetonitrile (w/v).

After completion of synthesis, the CPG was air dried and transferred to a 2 ml screw-cap microfuge tube. The oligonucleotide was deprotected and cleaved from the CPG with 2 ml ammonium hydroxide (25–30%). The tube was capped and incubated at room temperature for 20 minutes, then incubated at 55° C. for 7 hours. After deprotection was completed, the tubes were removed from the heat block and allowed to cool to room temperature. The caps were removed and the tubes were microcentrifuged at 10,000 rpm for 30 minutes to remove most of the ammonium hydroxide. The liquid was then transferred to a new 2 ml screw cap microcentrifuge tube and lyophilized on a Speed Vac concentrator (Savant, Farmingdale, N.Y.). After drying, the residue was dissolved in 400 μl of 0.3M NaCl and the DNA was precipitated with 1.6 ml of absolute EtOH. The DNA was pelleted by centrifugation at 14,000 rpm for 15 minutes, the supernatant decanted, and the pellet dried. The DNA was precipitated again from 0.1M NaCl as described above. The final pellet was dissolved in 500 μl $H_2O$ and centrifuged at 14,000 rpm for 10 minutes to remove any solid material. The supernatant was transferred to another microcentrifuge tube and the amount of DNA was determined spectrophotometrically. The concentration was determined by the optical density at 260 nm. The $E_{260}$ for the DNA portion of the oligonucleotide was calculated by using OLIGSOL (Lautenberger (1991) *Biotechniques* 10:778–780). The $E_{260}$ of the 2'-O-methyl portion was calculated by using OLIGO 4.0 Primer Extension Software (NBI, Plymouth, Minn.).

Oligonucleotide purity was checked by polyacrylamide gel electrophoresis (PAGE) and UV shadowing. 0.2 $OD_{260}$ units were loaded with 95% formamide/$H_2O$ and Orange G dye onto a 20% denaturing polyacrylamide gel (20 cm×20 cm). The gel was run until the Orange G dye was within one inch of the bottom of the gel. The band was visualized by shadowing with shortwave UV light on a thin layer chromatography plate (Keiselgel 60 F254, EM Separations, Gibbstown, N.J.).

Some oligonucleotides were synthesized without removing the 5'-trityl group (trityl-on) to facilitate reverse-phase HPLC purification. Trityl-on oligonucleotides were dissolved in 3 ml water and centrifuged at 6000 rpm for 20 minutes. The supernatant was filtered through a 0.45 micron syringe filter (Gelman Scientific, Ann Arbor, Mich.) and purified on a 1.5×30 cm glass liquid chromatography column (Spectrum, Houston, Tex.) packed with C-18 μBondapak chromatography matrix (Waters, Franklin, Mass.) using a 600E HPLC (Waters, Franklin, Mass.). The oligonucleotide was eluted at 5 ml/min with a 40 minute gradient from 14–32% acetonitrile (Baxter, Burdick and Jackson Division, Muskegon, Mich.) in 0.1M ammonium acetate (J. T. Baker, Phillipsburg, N.J.), followed by 32% acetonitrile for 12 minutes. Peak detection was done at 260 nm using a Dynamax UV-C absorbance detector (Rainin, Emeryville, Calif.).

The HPLC purified trityl-on oligonucleotide was evaporated to dryness and the trityl group was removed by incubation in 5 ml 80% acetic acid (EM Science, Gibbstown, N.J.) for 15 minutes. After evaporating the acetic acid, the oligonucleotide was dissolved in 3 ml 0.3M NaCl and ethanol precipitated. The precipitate was isolated by centrifugation and precipitated again with ethanol from 3 ml 0.1M NaCl. The precipitate was isolated by centrifugation and dried on a Savant Speed Vac (Savant, Farmingdale, N.Y.). Quantitation and PAGE analysis were performed as described above for ethanol precipitated oligonucleotides.

Standard phosphoramidite chemistry was applied in the synthesis of oligonucleotides containing methylphosphonate linkages using two Pharmacia Gene Assembler Special DNA synthesizers. One synthesizer was used for the synthesis of phosphorothioate portions of oligonucleotides using β-cyanoethyl phosphoramidites method discussed above. The other synthesizer was used for introduction of methylphosphonate portions. Reagents and synthesis cycles that had been shown advantageous in methylphosphonate synthesis were applied (Hogrefe et al., in *Methods in Molecular Biology*, Vol. 20: *Protocols for Oligonucleotides and Analogs* (Agrawal, ed.) (1993) Humana Press Inc., Totowa, N.J.). For example, 0.1M methyl phosphonamidites (Glen Research) were activated by 0.25M ethylthiotetrazole; 12 minute coupling time was used; oxidation with iodine (0.1M) in tetrahydrofuran/2,6-lutidine/water (74.75/25/0.25) was applied immediately after the coupling step; dimethylaminopyridine (DMAP) was used for the capping procedure to replace standard N-methylimidazole (NMI). The chemicals were purchased from Aldrich (Milwaukee, Wis.).

The work up procedure was based on a published procedure (Hogrefe et al. (1993) *Nucleic Acids Res.* 21:2031–2038). The product was cleaved from the resin by incubation with 1 ml of ethanol/acetonitrile/ammonium hydroxide (45/45/10) for 30 minutes at room temperature. Ethylenediamine (1.0 ml) was then added to the mixture to deprotect at room temperature for 4.5 hours. The resulting solution and two washes of the resin with 1 ml 50/50 acetonitrile/0.1M triethylammonium bicarbonate (TEAB), pH 8, were pooled and mixed well. The resulting mixture was cooled on ice and neutralized to pH 7 with 6N HCl in 20/80 acetonitrile/water (4–5 ml), then concentrated to dryness using the Speed Vac concentrator. The resulting solid residue was dissolved in 20 ml of water, and the sample desalted by using a Sep-Pak cartridge. After passing the aqueous solution through the cartridge twice at a rate of 2 ml per minute, the cartridge was washed with 20 ml 0.1M TEAB and the product eluted with 4 ml 50% acetonitrile in 0.1M TEAB at 2 ml per minute. The eluate was evaporated to dryness by Speed Vac. The crude product was purified by polyacrylamide gel electrophoresis (PAGE), desalted using a Sep-Pak cartridge. The oligonucleotide was ethanol precipitated from 0.3M NaCl, then 0.1M NaCl. The product was dissolved in 400 μl water and quantified by UV absorbance at 260 nm.

2. Luciferase Assay Using Stably Transfected Cells

A. HBV Antisense Target Constructs

All sequences were derived from HBV subtype ayw (GenBank accession #J02203) as described by Galibert et al. (*Nature,* (1979) London, 281:646–650).

The HBV polymerase-luciferase fusion pGLpol construct (FIG. 10) was prepared by inserting 35 nucleotides spanning the translation start site of HBVayw polymerase gene (nt 2294–2328) between the cytomegalovirus immediate early gene promoter and luciferase reporter gene in the plasmid pGLori (Roche, Nutley, N.J.).

Three different HBV-luciferase fusion constructs were generated incorporating the region around the HBV subtype ayw epsilon region (FIG. 10). The pGLE construct consists of 71 nucleotides representing the epsilon stem loop region alone (nt 1843–1913) inserted between the cytomegalovirus immediate early gene promoter and luciferase reporter gene in the plasmid pGLori. Translation in this construct should initiate at the HBV core gene initiation site (nt 1903).

The constructs pGLE2 and pGLE3 are shown in FIG. 10. The constructs consist of 130 nucleotides representing the precore translation start site and epsilon stem loop region (nt 1813–1943) inserted between the cytomegalovirus immediate early gene promoter and luciferase reporter gene in the plasmid pGLori. In these two constructs the translation start site of the luciferase gene was removed. In addition, the HBV core gene translation start site was mutated in pGLE3 (nt 1904 T>C). A complementary mutation was introduced at nt 1854 (A>G) to maintain the base pairing in the epsilon stem. In pGLE2 translation can be initiated from the precore or core translation start site. In pGLE3 translation can only be initiated at the precore translation start site.

The plasmid pHBVE+ was generated by subcloning a StuI, BamHI fragment from the plasmid pAM6 (ATCC Ac. No. 45020, American Type Culture Collection, Rockville, Md.), representing HBV subtype adw nt 1701- nt 34 (GenBank accession #V00866) (Ono et al. (1983) *Nucleic Acids Res.* 11:1747–1757), into pBluescript II SK(+) (Stratagene, La Jolla, Calif.). This construct was used in RNase H studies.

B. Generation of Stably Transfected Cell Lines

The HBV subtype ayw-luciferase gene constructs described above were subcloned by polymerase chain reaction from the respective plasmids and the parent plasmid pGLori into the vector pCR-Script (Stratagene, La Jolla, Calif.), and further subcloned into the vector pcDNA3 (Invitrogen, San Diego, Calif.). These constructs were stably transfected using Lipofectamine (GIBCO-BRL, Gaithersburg, Md.) into HepG2 cells (ATCC Ac. No. HB 8065, American Type Culture Collection, Rockville, Md.; U.S. Pat. No. 4,393,133). Several Geneticin (GIBCO-BRL, Gaithersburg, Md.)—resistant, luciferase-expressing clones were selected at random for each construct.

C. Antisense Oligonucleotide Assays

Stably transfected HepG2 cells were seeded into 96 well plates. Lipofectin (GIBCO-BRL, Gaithersburg, Md.) was diluted to a concentration of 10 $\mu$g/ml in Optimem serum-free medium (GIBCO-BRL, Gaithersburg, Md.), and 100 $\mu$l dispensed into each well of the 96 well plate. Oligonucleotides were diluted to 5 $\mu$M or 25 $\mu$M in 10 $\mu$g/ml Lipofectin in Optimem, and 25 $\mu$l dispensed into three wells of the 96 well plate. The oligonucleotide was serially diluted in five fold increments down the plate. The plates were incubated overnight at 37° C. Cells were washed twice with Dulbecco's phosphate-buffered saline (PBS) and lysed in 50 $\mu$l cell lysis buffer (Analytical Luminescence Laboratory, San Diego, Calif.). Luciferase activity was measured in 20 $\mu$l lysate using Analytical Luminescence Laboratory substrates in a MicroLumat LB 96 P luminometer (EG&G Berthold, Nashua, N.H.).

3. RNase H Cleavage Assay

A. Preparation of Labelled RNA

Uniformally $^{32}$P-labelled RNA was prepared from 1 $\mu$g linearized plasmid using the Ambion MEGAscript In Vitro Transcription Kit (Ambion, Inc., Austin, Tex.) according to the manufacturers' instructions, using [$\alpha^{32}$P]CTP as the radioactive label. The RNA was treated with RNase-free DNase I (Ambion, Inc., Austin, Tex.), extracted with phenol:chloroform:isoamyl alcohol (25:24:1) and purified from nucleotides and nucleosides on a G-50 Sephadex spin column (Boehringer-Mannheim, Indianapolis, Ind., or Pharmacia, Uppsala, Sweden).

5' end-labelled RNA was prepared from 1 $\mu$g linearized plasmid using the Ambion MEGAscript In Vitro Transcription Kit (Ambion, Inc., Austin, Tex.) according to the manufacturers' instructions, except that the GTP concentration was lowered to 6 mM, and 6 mM guanosine hydrate was added to the transcription mix. The RNA was treated with RNase-free DNase I (Ambion, Inc., Austin, Tex.), extracted with phenol:chloroform:isoamyl alcohol (25:24:1) and purified from nucleotides and nucleosides on a G-50 Sephadex spin column (Boehringer-Mannheim, Indianapolis, Ind., or Pharmacia, Uppsala, Sweden). The RNA was end-labelled with [$\alpha^{32}$P]ATP (Amersham, Arlington Heights, Ill.) and T4 polynucleotide kinase (Pharmacia, Uppsala, Sweden) according to the enzyme manufacturers' instructions. The labelled RNA was purified from nucleosides and nucleotides on a G-50 Sephadex spin column (Boehringer-Mannheim, Indianapolis, Ind., or Pharmacia, Uppsala, Sweden) and stored at −80° C. until needed.

B. RNase H Cleavage with Random 20 mer Library

End-labelled RNA (20–100 nM) was incubated with a 20 base random DNA library (50–100 $\mu$M) (synthesized on Pharmacia Gene Assembler, as described above), boiled previously to dissociate any aggregates, for 90 min at 37° C. in 9 $\mu$l 1×buffer (40 mM Tris-HCl pH 7.4, 4 mM MgCl$_2$, 1 mM DTT). RNase H (Boehringer-Mannheim, Indianapolis, Ind.) (1 $\mu$l, 1 unit/$\mu$l) was then added. The reaction was incubated at 37° C. for 10 min, quenched by addition of 10 $\mu$l 90% formamide containing 0.1% phenol red/0.1% xylene cyanol, and frozen on dry ice. The quenched reactions were boiled for 2.5 to 3 minutes, quenched on ice, and 5 to 7 $\mu$l loaded onto a denaturing 4% polyacrylamide gel prerun to 50° to 55° C. The phenol red was typically run to the bottom of the gel, which was then dried at 80° C. under vacuum. The gel was autoradiographed using XOMAT film (Kodak, Rochester, N.Y.) or analyzed using phosphorimage technology on a Molecular Dynamics (Sunnyvale, Calif.) or Bio Rad Phosphorimager (Hercules, Calif.).

C. Cleavage of HBV RNA with Semirandom Oligonucleotides

Semirandom oligonucleotides (100 $\mu$M in H$_2$O) were boiled for 1 min to dissociate any aggregates formed between complementary sequences in the mix and 1 $\mu$l (final concentration 10 $\mu$M) was added to 8 $\mu$l 1×RNase H buffer (40 mM Tris-HCl pH 7.4, 4 mM MgCl$_2$, 1 mM DTT) containing end-labelled RNA (20–100 nM). After a 15 minute preincubation at 37° C., RNase H was added (1 U) and incubated for 10 min at 37° C. The reactions were quenched and analyzed as described above. Sites of cleavage were estimated using DNA and/or RNA molecular size markers.

D. Cleavage of HBV RNA with Specific Antisense Oligonucleotides

In 9 $\mu$l 1×RNase H buffer (40 mM Tris-HCl pH 7.4, 4 mM MgCl$_2$, 1mM DTT), 20–100 nM labelled RNA and 100 nM oligonucleotides were preincubated for 15 min at 37° C. 1 $\mu$l RNase H (1 U/$\mu$l) was added, and the reaction was incubated at 37° C. for 10 min. The reactions were quenched and analyzed as described above.

Quantitation of the cleavage products was performed using software supplied with the Phosphorimager (Molecular Dynamics, Sunnyvale, Calif., or Bio-Rad Laboratories, Hercules, Calif.). "Counts" were determined by drawing a box around the band of interest and subtracting the background determined with a box drawn nearby. Counts in a product band were compared to total counts in the lane above that band to determine % cleavage.

4. HBV Encapsidation Assay

The assay is essentially identical to that described in Pollack et al. (*J. Virol.* (1993) 67:3254–3263). Briefly, HepG2 cells are transfected with the plasmids pCMV-CP and pE-LacZ (Dr. D. Ganem, University of California Medical Center, San Francisco, Calif.) by calcium phosphate precipitation. The HepG2 cells are treated with 0–10 $\mu$M antisense oligonucleotides pre- or post-transfection. Three days after transfection the cells are harvested and total cell RNA is prepared using Trizol reagent (GIBCO-BRL, Gaithersburg, Md.). Alternatively, HBV core particles are collected from cytoplasmic extracts after nuclease digestion by polyethylene glycol precipitation. The encapsidated RNA is extracted from the core particles using Trizol reagent (GIBCO-BRL, Gaithersburg, Md.).

The relative amounts of E-LacZ RNA in total cell RNA and encapsidated in core particles are assessed using a ribonuclease protection assay (RPA) (Ambion, Austin, Tex.) using RNase T1. The RNA probe used is transcribed by T7 polymerase (Ambion, Austin, Tex.) from the plasmid pLacProbe. The plasmid pLacProbe was constructed by subcloning a 425 bp Mlu I fragment from pE-LacZ into the vector pGEM3z (Promega, Madison, Wis.). Data from the RPA is quantitated using a BioRad GS250 Phosphorimager (BioRad, Hercules, Calif.).

5. Studies of Oligonucleotide Anti-Viral Activity by Southern Hybridization Analysis A. Cell Culture The cell line HepG2.2.15 (Sells et al. (1988) *J. Virol.* 62:2836–2844) was routinely cultured in RPMI.1640 medium (Life Technologies Ltd., Paisley, Scotland) supplemented with 10% fetal bovine serum (FBS), 100 U/ml penicillin, and 150 $\mu$g/ml streptomycin. Cultures were replaced after 10 passages with cells freshly cultured from a mycoplasma-free frozen stock. Cultures were maintained at 37° C. in a humidified atmosphere of 5% $CO_2$ in air.

Cells were cultured in 6-well plates at $10^6$ cells/well in 4 ml medium (RPMI.1640 as above but supplemented with 5% FBS) and maintained as above. After 2 days, the medium was replaced with fresh medium containing 3% FBS and antiviral compound. For antisense experiments, cells were treated with a series of five 3-fold dilutions from a starting concentration of 10 $\mu$M. Cultures with 3TC were treated in a similar fashion but with an initial concentration of 1.0 $\mu$M. The cultures were maintained for 10 days, during which medium and compound was replaced after 3, 5 and 7 days. Cells were washed once with Hanks balanced salt solution (HBSS) immediately prior to each replacement. After 10 days, the cells were washed twice with HBSS and treated overnight at 37° C. with 0.55 ml lysis buffer (10 mM Tris. HCl pH 7.5; 5 mM EDTA; 150 mM NaCl; 1.0% w/v sodium dodecyl sulphate) containing 100 $\mu$g/ml proteinase K. The lysate was harvested, treated for 1 hour at 60° C., and extracted once with phenol/chloroform and twice with chloroform before precipitation twice with ethanol. The dried precipitate was resuspended in 50 $\mu$l TE buffer (10 mM Tris-HCl, pH 8.0; 1 mM EDTA) and allowed to dissolve overnight at 4° C. The solution was then assayed for DNA by spectrophotometric measurement at 260 nm. Yields were of the order of 40 to 100 $\mu$g with 260/280 ratios within the range 1.5 to 2.0.

B. Electrophoresis and Blotting

DNA obtained from HepG2.2 15 culture was digested in 20 $\mu$g amounts in 30 $\mu$l buffer E with 10 units of HindIII (Promega Limited, Southampton, U.K.) overnight at 37° C. The DNA fragments were separated by agarose gel electrophoresis on 0.8% gels run in 0.5×TBE at 50 volts overnight. Gels were then treated serially with 0.25M HCl for 20 minutes; 0.5M NaOH in 1.0M NaCl for 45 minutes, and finally with 0.5M Tris-HCl, pH 7.0, and 1.0M NaCl for 30 minutes, all at room temperature with gentle shaking. The gels were rinsed with 6×SSC and the DNA blotted overnight onto nylon membranes (Hybond N; Amersham International, Bucks, U.K.) by capillary action. The membranes were washed with 6×SSC for 5 minutes and dried before UV cross-linking using a Stratalinker (StrataGene Limited, Cambridge, U.K.). The blots were stored at 4° C. until hybridized.

C. Preparation of Southern Hybridization Probe

A full length HBV genome fragment was prepared from the plasmid pCH3/3097 (Bartenschlager et al. (1992) *Nucleic Acids Res.* 20:195–202) by means of excision with restriction endonucleases HindIII, SacI and PvuI in buffer C (Promega Limited, Southampton, U.K.), followed by agarose gel electrophoresis purification. This fragment was used to produce the labelled probe by random-primed DNA synthesis in the presence of $^{32}$P-dCTP (Amersham AA0005 [$\alpha^{32}$P]dCTP 110 TBq/mmol (3000 Ci/mmol), in stabilized aqueous solution with dye) using the "Megaprime" kit (Amersham International, Bucks, U.K.). A starting amount of 25 ng HBV DNA was labelled to an estimated specific activity of $1-2\times10^9$ dpm/$\mu$g DNA.

D. Hybridization

Membranes were pre-hybridized with formamide solution supplemented with 100 $\mu$g/ml heat-denatured salmon-sperm DNA(Sigma-Aldrich, Poole, U.K.) in a hybridization oven at 42° C. for at least 3 hours. The solution was replaced with fresh formamide solution (10.0 ml) supplemented with salmon-sperm DNA as before and freshly prepared $^{32}$P-labelled probe. Incubation was continued for a further 16–20 hours. The probe was removed and the membranes washed with 2×SSC supplemented with 0.1% (w/v) SDS twice for 15–30 minutes at 65° C. Washes were repeated with 1×SSC and 0.5×SSC all supplemented with 0.1% SDS. The blots were examined for background label using a Mini Monitor (MiniInstruments Ltd., Burnham-on-Crouch, U.K.) and, if further washes were not required, the membranes were dried, wrapped with plastic film (Saran Wrap), and placed in a cassette for phosphorimaging (Molecular Dynamics, Sunnyvale, Calif.).

E. Analysis

After 1–3 days exposure, results were obtained using a Phosphorimager (Molecular Dynamics Inc., Sunnyvale, Calif.). Analysis was carried out using ImageQuant software (Molecular Dynamics Inc., Sunnyvale, Calif.). Those bands representing integrated DNA (10 kb) and completed replicative intermediate (RI—3.8 kb), as described by Sells et al. (*J. Virol.* (1988) 84:1005–1009), were identified by reference to a marker lane containing a 1 kb DNA ladder. The amount of replicative intermediate present relative to integrated DNA was calculated (3.8 kb DNA/10.2 kb DNA) and percent inhibition calculated according to the formula:

$$\% \text{ inhibition} = 100 - \left\{ \left\{ \frac{\text{relative amount of } RI \text{ in treated culture}}{\text{relative amount of } RI \text{ in untreated culture}} \right\} \times 100 \right\}$$

The concentration of compound which produced 50% inhibition of RI formation ($IC_{50}$) was determined graphically.

6. Kinetic PCR Protocol for HBV Anti-Viral Assay

The anti-viral assay was performed using HepG 2.2.15 cells (Sells et al. (1986) *Proc. Natl. Acad. Sci.* (USA) 84:1005–1009) seeded at a density of $1\times10^5$ per well in 24 well plates. The cells were grown to confluence and allowed to stabilize for 2–3 days in RPMI media (supplemented with 10% fetal calf serum (FCS), 2 mM glutamine and penstrep (Life Technologies Ltd., Paisley, Scotland) prior to the addition of the oligonucleotide (defined as day 0). Six dilutions (10, 5, 1, 0.5, 0.1, and 0 $\mu$M) were set up in duplicate for each of the antisense oligonucleotides. In each assay run, the nucleoside analog, $\beta$-L-(2R,5S)-1,3 oxathiolanyl cytosine (3TC) (Glaxo, Greenford, U.K.) was included as positive control at 0.5, 0.1, 0.075, 0.05, and 0.01 and 0 μM in duplicate. Oligonucleotide was added to 1 ml of RPMI media (supplemented with 3% FCS, 2 mM glutamine and penstrep) at each of the indicated dilutions. At days 2, 4 and 7, the old media was removed and replaced with fresh media containing compound. At day 10, the supernatants were harvested, clarified by low speed centrifugation, prior to the addition of Triton X100 (Sigma, St. Louis, Mo.) and tri-n-butyl phosphate to give a final concentration of 1%. The samples were then heated to 70° C. for 20 minutes to disrupt the viral particles.

Following this treatment, the viral particles were subject to analysis by kinetic PCR. The primers RJ407 (SEQ ID NO:51) and RJ431 (SEQ ID NO:52) were used to detect a 205 bp fragment of the core gene. Kinetic PCR was performed essentially as described by Higuchi et al. (*Biotechnol.* (1993) 11:1026–1030). Briefly, the PCR reactions were set up under standard conditions except that ethidium bromide was included at a concentration of 4 μg/ml. After each PCR cycle, the samples were illuminated with UV light at 302 nm, and a picture was taken using a computer controlled, cooled CCD video camera with the lens focused on the surface of the thermocycler block. A kinetic PCR analysis was performed by plotting the average intensity of fluorescence from each PCR sample after each annealing/extension cycle against the cycle number. The original template concentration can be calculated by utilizing a standard fluorescence curve generated by templates of known concentration.

7. In vitro Translation Assays

A. Construction of pHBVpol

Figure 13:
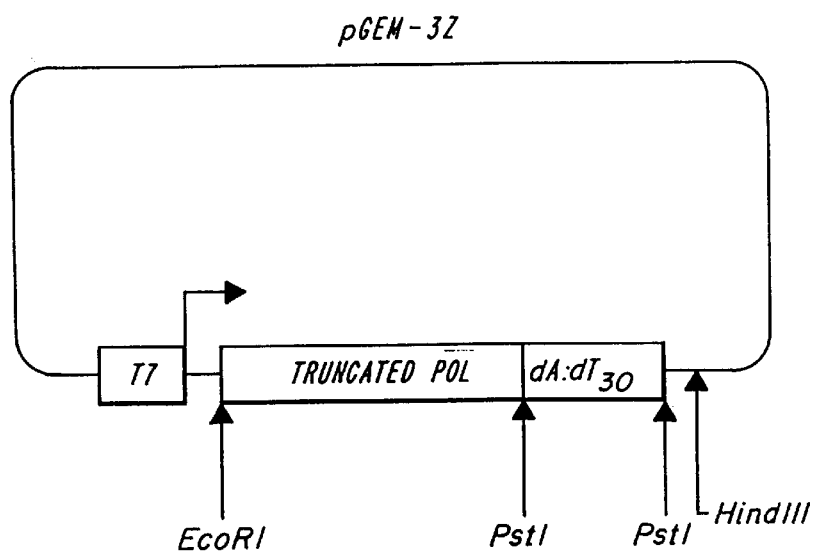
FIG. 13 is a diagrammatic representation of the map of pHBVpol.

The 5' end of the polymerase gene (pol) open reading frame, nt 2292–2942, was amplified by the PCR from the full length HBV clone pCH3/3097 (Bartenschlager et al. (1992) *Nucleic Acids Res.* 20:195–202). The 5' amplification primer AS10 (SEQ ID NO:55) encoded an EcoRI site. The 3' amplification primer AS11 (SEQ ID NO:56) both encoded a PstI site and introduced a stop codon in the place of a leucine codon at position 2942–2944. The PCR product was digested with EcoRI and PstI (Promega, Madison, Wis.) and inserted into similarly digested plasmid vector pGEM-3z (Promega, Madison, Wis.). The resulting recombinant plasmid was recut with PstI and an oligonucleotide dA:dT$_{(30)}$ linker was introduced. A sketch map of pHBVpol is shown in FIG. 13.

B. In vitro Transcription of RNA pHBVpol and a second plasmid pHSVProt were linearized with HindIII (Promega, Madison, Wis.), RNA was in vitro transcribed from each construct using T7 Cap-Scribe reagents (Boehringer-Mannheim, Indianapolis, Ind.) employed as per the manufacturer's instructions. The quantity and quality of the RNA's was assessed on a 2% agarose/formaldehyde gel. The control HSVProt RNA was arbitrarily diluted 10 fold to 200 ng/μl and stored in 20 μl aliquots at −80° C.

C. Assessment of Antisense Activity of Pol Oligonucleotides

The sequences of all oligonucleotides used in these experiments are shown in Table 1. In this series of experiments only phosphodiester (PO) oligonucleotides were used. 5 μM, 2.5 μM, and 1.25 μM stocks of each of HBVpol-1, HBVpol-2, HBVpol-3, and randomer were made up and stored frozen. Reactions were set up using 100 ng HBVpol and 200 ng pHSVprot. The volume of water in the translation master mix was reduced to allow the addition of 1 μl of each dilution of each oligonucleotide to the reactions whilst maintaining the final volume at 12 μl. This corresponds to final oligonucleotide concentrations of approximately 400 nM, 200 nM, and 100 nM.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A synthetic oligonucleotide complementary to at least two noncontiguous regions of a hepatitis B virus (HBV) nucleic acid, the oligonucleotide being 20–30 nucleotides in length.

2. A synthetic oligonucleotide complementary to at least two noncontiguous regions in the epsilon region of the precore gene.

3. The synthetic oligonucleotide of claim 1 which is modified.

4. The oligonucleotide of claim 3 wherein the modification comprises at least one internucleotide linkage selected from the group consisting of alkylphosphonate, phosphorothioate, phosphorodithioate, alkylphosphonothioate, phosphoramidate, carbamate, carbonate, phosphate triester, acetamidate, carboxymethyl ester, and combinations thereof.

5. The oligonucleotide of claim 4 comprising at least one phosphorothioate internucleotide linkage.

6. The oligonucleotide of claim 5 having phosphorothioate internucleotide linkages.

7. The oligonucleotide of claim 5 comprising at least one 2'-O-methyl.

8. The oligonucleotide of claim 1 comprising at least one deoxyribonucleotide.

9. The oligonucleotide of claim 8 comprising at least one ribonucleotide.

10. The oligonucleotide of claim 9 comprising at least one 2'-O-methyl.

11. The oligonucleotide of claim 1 comprising a sequence selected from the group consisting of SEQ ID NOS:32–41.

12. The synthetic oligonucleotide of claim 11 having SEQ ID NO:32.

13. The synthetic oligonucleotide of claim 11 having SEQ ID NO:33.

14. The synthetic oligonucleotide of claim 11 having SEQ ID NO:34.

15. The synthetic oligonucleotide of claim 11 having SEQ ID NO:35.

16. The synthetic oligonucleotide of claim 11 having SEQ ID NO:36.

17. The synthetic oligonucleotide of claim 11 having SEQ ID NO:37.

18. The synthetic oligonucleotide of claim 11 having SEQ ID NO:38.

19. The synthetic oligonucleotide of claim 11 having SEQ ID NO:39.

20. The synthetic oligonucleotide of claim 11 having SEQ ID NO:40.

21. The synthetic oligonucleotide of claim 11 having SEQ ID NO:41.

* * * * *